(12) United States Patent
Khurana et al.

(10) Patent No.: US 11,602,722 B2
(45) Date of Patent: Mar. 14, 2023

(54) MICROFLUIDIC DROPLET GENERATORS

(71) Applicant: Illumina, Inc., San Diego, CA (US)

(72) Inventors: Tarun Kumar Khurana, Fremont, CA (US); Foad Mashayekhi, San Francisco, CA (US); Hei Ka Patrick Tam, San Ramon, CA (US)

(73) Assignee: ILLUMINA, INC., San Diego, CA (US)

( * ) Notice: Subject to any disclaimer, the term of this patent is extended or adjusted under 35 U.S.C. 154(b) by 436 days.

(21) Appl. No.: 16/780,104

(22) Filed: Feb. 3, 2020

(65) Prior Publication Data
US 2020/0246771 A1   Aug. 6, 2020

Related U.S. Application Data

(60) Provisional application No. 62/800,981, filed on Feb. 4, 2019.

(51) Int. Cl.
*B01J 13/14* (2006.01)
*B01L 3/00* (2006.01)
*C12Q 1/6806* (2018.01)

(52) U.S. Cl.
CPC ......... *B01J 13/14* (2013.01); *B01L 3/502792* (2013.01); *C12Q 1/6806* (2013.01);
(Continued)

(58) Field of Classification Search
CPC .... B01J 13/14; B01J 13/0052; B01J 13/0069; B01L 3/502792; B01L 2200/0673;
(Continued)

(56) References Cited

U.S. PATENT DOCUMENTS 2,192,094 A   2/1940  Moore
9,133,009 B2  9/2015  Baroud et al.
(Continued)

FOREIGN PATENT DOCUMENTS

CN   102272763 A   12/2011
CN   104607257 A    5/2015
(Continued)

OTHER PUBLICATIONS

Dangla, et al., "Droplet microfluidics driven by gradients of confinement" Proc. Nat'l Acad. Sci. U.S.A 110 (3), 853-858, 2003.
(Continued)

*Primary Examiner* — Narayan K Bhat
(74) *Attorney, Agent, or Firm* — Marshall, Gerstein & Borun LLP

(57) ABSTRACT

Disclosed herein is a novel method of producing monodisperse aqueous droplets, as well as a novel microfluidic droplet generator. In some examples, the method comprises flowing an aqueous solution through a microchannel and into a sample reservoir of the microfluidic droplet generator, wherein monodisperse droplets of the aqueous solution form by step-emulsification at a step change in height at an intersection of a reservoir end of the microchannel and a sidewall of the sample reservoir. In some examples, the aqueous solution is a hydrogel precursor solution and monodisperse droplets of the hydrogel precursor solution form by step-emulsification at the step change in height at the intersection of the reservoir end of the microchannel and the sidewall of the sample reservoir. In some examples, the monodisperse droplets of the hydrogel precursor solution are incubated under conditions suitable for gelation to form hydrogel beads.

26 Claims, 13 Drawing Sheets

(52) U.S. Cl.
CPC . *B01L 2200/0673* (2013.01); *B01L 2300/047* (2013.01); *B01L 2300/0858* (2013.01); *B01L 2400/0403* (2013.01); *B01L 2400/084* (2013.01)

(58) Field of Classification Search
CPC ....... B01L 2300/047; B01L 2300/0858; B01L 2400/0403; B01L 2400/084; B01L 3/0275; B01L 2200/027; B01L 2400/0487; B01L 3/502784; C12Q 1/6806
See application file for complete search history.

(56) References Cited

U.S. PATENT DOCUMENTS

| | | | |
|---|---|---|---|
| 9,138,700 | B2 | 9/2015 | Van Dam et al. |
| 9,289,787 | B2 | 3/2016 | Doak et al. |
| 2004/0115830 | A1 | 6/2004 | Touzov |
| 2008/0023330 | A1* | 1/2008 | Viovy ............... B01L 3/502784 204/600 |
| 2014/0194324 | A1 | 7/2014 | Gormley et al. |
| 2015/0298091 | A1* | 10/2015 | Weitz .................. B01F 33/3011 506/28 |
| 2015/0368638 | A1 | 12/2015 | Steemers et al. |
| 2018/0056294 | A1 | 3/2018 | Di Carlo et al. |
| 2018/0155709 | A1 | 6/2018 | Gormley et al. |

FOREIGN PATENT DOCUMENTS

| | | |
|---|---|---|
| CN | 107109319 A | 8/2017 |
| CN | 108905914 A | 11/2018 |
| EP | 3 120 927 A1 | 1/2017 |
| WO | 2011/090396 | 7/2011 |
| WO | 2016/130704 | 8/2016 |
| WO | WO-2018/140966 A1 | 8/2018 |

OTHER PUBLICATIONS

Eggersdorfer, et al., "Wetting controls of droplet formation in step emulsification" Proc. Nat'l Acad. Sci. U.S.A. 115 (38), 9479-9484, 2018.

Ofner, et al., "High-throughput step emulsification for the production of functional materials using a glass microfluidic device" Macromolecular chemistry and physics 218 (2), 1600472, 2017.

Postek, et al., "A passive microfluidic system based on step emulsification allows the generation of libraries of nanoliter-sized droplets from microliter droplets of varying and known concentrations of a sample" Lab on a Chip 17 (7), 1323-1331, 2017.

Stolovicki, et al., "Throughput enhancement of parallel step emulsifier devices by shear-free and efficient nozzle clearance" Lab on a Chip 18 (1), 132-138, 2018.

Sugiura, et al., "Preparation of monodispersed solid lipid microspheres using a microchannel emulsification technique" Journal of colloid and interface science 227 (1), 95-103, 2000.

Wen et al., "Microfluidic fabrication of microparticles for biomedical applications", Chemical Society Reviews, vol. 47, No. 15, pp. 5646-5683 (Jan. 2018).

\* cited by examiner

Hydroge | beads: mean size 123 μm (Std: 6 μm)

MICROFLUIDIC DROPLET GENERATORS

CROSS-REFERENCE TO RELATED APPLICATIONS

This application claims the benefit of U.S. Provisional Patent Application 62/800,981, filed on Feb. 4, 2019, the content of which is incorporated by reference herein in its entirety and for all purposes.

BACKGROUND

To generate aqueous droplets, typical methods utilize a microfluidic droplet generator involving multiple syringe pumps or a pressurized air or vacuum source to drive at least two different liquids, one aqueous-based (the disperse phase) and one oil-based (the continuous phase), via at least two inlets and through cross-channels of the device. Such methods are expensive and complicated.

SUMMARY

A method of producing monodisperse aqueous droplets is provided herein. The method comprises providing a microfluidic droplet generator comprising a body having a single inlet fluidly connected to a microchannel fluidly connected to a sample reservoir. The sample reservoir comprises a floor and a sidewall, and contains a reservoir fluid that is immiscible in water. The microchannel comprises an inlet end and a reservoir end. The reservoir end of the microchannel intersects the sidewall of the sample reservoir at a location submerged beneath the reservoir fluid. In some examples, a longitudinal axis of the microchannel is substantially parallel to the ground and substantially perpendicular to the sidewall of the sample reservoir. The method further comprises flowing an aqueous solution into the inlet, through the microchannel, and into the sample reservoir by applying pressure on the aqueous solution at the inlet. Monodisperse droplets of the aqueous solution form by step-emulsification at a step change in height at the intersection of the reservoir end of the microchannel and the sidewall of the sample reservoir.

In some examples, the pressure on the aqueous solution at the inlet is applied with a manual or electric air-displacement micropipette. In some examples, a fluidic resistance of the microchannel prevents jetting of the aqueous solution into the sample reservoir at the reservoir end of the microchannel when the pressure is applied to the aqueous solution at the inlet, for example, when pressure is applied with a manual or electric air-displacement micropipette.

In some examples, the aqueous solution comprises genetic material (such as genomic DNA or single cells containing genomic DNA), and the genetic material is encapsulated within the monodisperse droplets of the aqueous solution formed by step-emulsification at the step change in height at the intersection of the reservoir end of the microchannel and the sidewall of the sample reservoir.

In some examples, the method further comprises producing hydrogel beads. In such examples, the aqueous solution is a hydrogel precursor solution, the monodisperse droplets of the aqueous solution are monodisperse droplets of the hydrogel precursor solution, and the method further comprises incubating the monodisperse droplets of the hydrogel precursor solution under conditions suitable for gelation to form the hydrogel beads. In some such examples, the hydrogel precursor solution comprises hydrogel polymer and crosslinker and does not comprise a gelation catalyst for the hydrogel polymer and crosslinker, and incubating the monodisperse droplets of the hydrogel precursor solution under conditions suitable for gelation comprises incubating the monodisperse droplets of the hydrogel precursor solution with the gelation catalyst to initiate gelation of the hydrogel polymer and crosslinker to form the hydrogel beads. In some such examples, the sample reservoir fluid comprises the gelation catalyst and the monodisperse droplets of the hydrogel precursor solution undergo gelation in the sample reservoir to form the hydrogel beads.

In some examples, the hydrogel precursor solution comprises genetic material (such as genomic DNA or single cells containing genomic DNA), and the genetic material is encapsulated within the hydrogel beads formed from the hydrogel precursor solution.

In some examples wherein the method comprises producing hydrogel beads, the method further comprises linking an outer surface of the hydrogel beads to a transposome complex.

Also provided herein is a microfluidic droplet generator that can be used, for example, in the disclosed method of producing monodisperse aqueous droplets.

It should be appreciated that all combinations of the foregoing concepts and additional concepts discussed in greater detail below (provided such concepts are not mutually inconsistent) are contemplated as being part of the inventive subject matter disclosed herein.

The foregoing and other features and advantages of this disclosure will become more apparent from the following detailed description of several examples which proceeds with reference to the accompanying figures.

BRIEF DESCRIPTION OF THE DRAWINGS

FIG. 16A shows a microfluidic droplet generators having a single microfluidic channel, and FIG. 16B shows a microfluidic droplet generator with multiple microfluidic channels.

DETAILED DESCRIPTION

In one example, the present disclosure provides a novel method of producing monodisperse aqueous droplets and hydrogel beads that is unexpectedly simple and easy to use.

Using the disclosed method, monodisperse aqueous droplets may be produced using a novel microfluidic droplet generator having a single inlet and a single flow along one or more microchannels. As discussed in more detail herein, in some examples, the aqueous solution is a hydrogel precursor solution and the method is used to generate monodisperse droplets of the hydrogel precursor solution. In the disclosed method, aqueous solution (the disperse phase) is loaded into the microfluidic droplet generator at the inlet, flows through the one or more microchannels, and exits into a sample reservoir containing a reservoir fluid that is immiscible in water (the continuous phase). The disclosed method utilizes step emulsification, which relies on a height change in the microchannel to pinch off a droplet from the microchannel, to generate the monodisperse droplets of aqueous solution.

A "monodisperse aqueous droplet," as used herein, is an isolated portion of an aqueous fluid that is completely surrounded by a second fluid that is immiscible in water. In some cases, the monodisperse aqueous droplets may be spherical or substantially spherical; however, in other cases, the monodisperse aqueous droplets may be non-spherical, for example, the monodisperse aqueous droplets may have the appearance of "blobs" or other irregular shapes, for instance, depending on the external environment.

Unlike traditional microfluidic droplet generators that have multiple inlets and flows for the aqueous (disperse) and oil (continuous) phases, and often multiple syringe pumps or a pressurized air or vacuum source to drive flow of the different phases through a cross-channeled microfluidic device, the method provided in one example herein utilizes a microfluidic droplet generator with only one inlet and a single flow along one or more microchannels.

Figure 1:
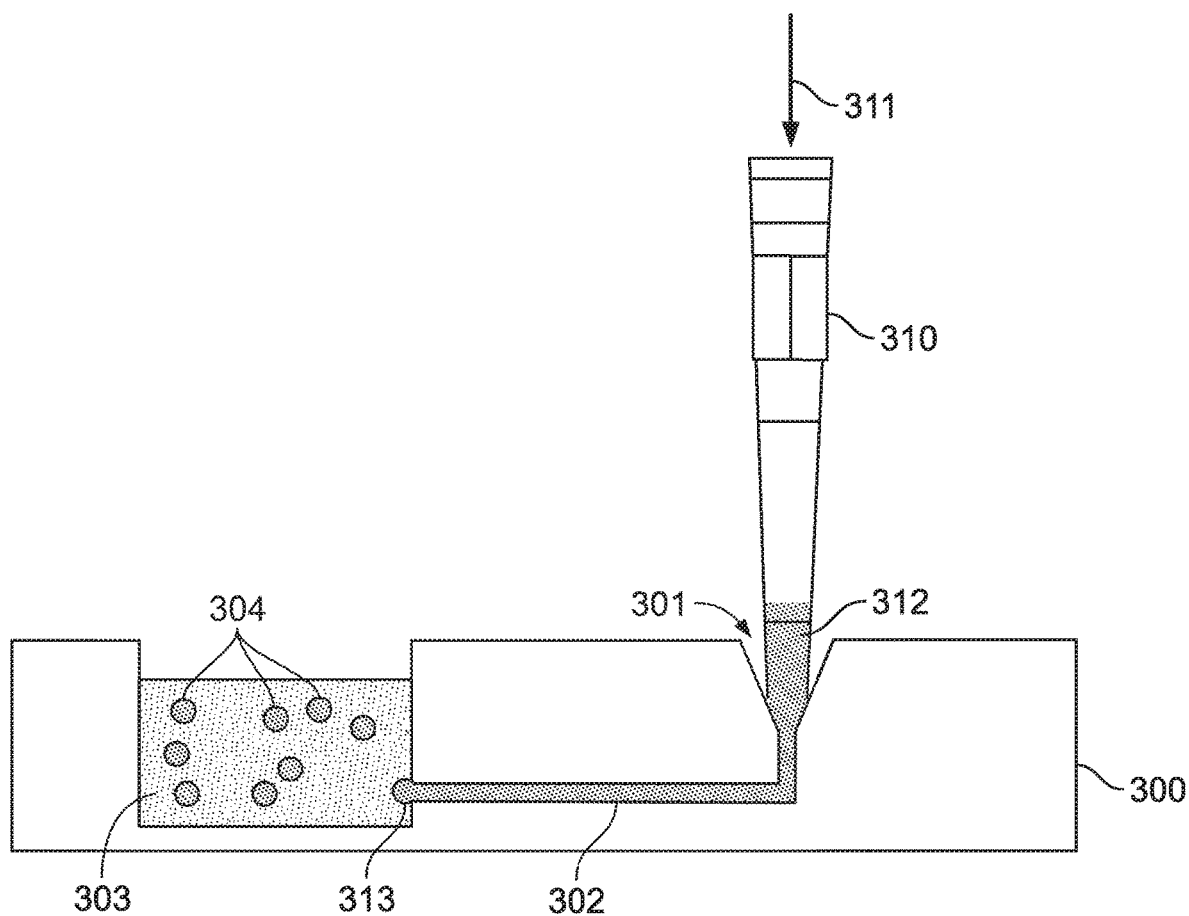
FIG. 1 is a schematic illustration of an example of the disclosed method for producing monodisperse aqueous droplets.

An implementation of the disclosed method is depicted in FIG. 1. As depicted, aqueous solution 312 is loaded into a pipette tip 310, which is inserted into an inlet 301 of a microfluidic droplet generator 300 as disclosed herein. Pressure 311 is applied to the aqueous solution 312 in the pipette tip 310 using a manual or electric micropipette connected to the pipette tip 310 to induce flow of the aqueous solution 312 through the inlet 301 and microchannel 302 and into a sample reservoir. The sample reservoir contains reservoir fluid 303 that is immiscible in water. Monodisperse droplets 304 of the aqueous solution form by step emulsification 313 at the intersection of the reservoir end of the microchannel 302 and the sample reservoir and undergo gelation in the sample reservoir to form the hydrogel beads.

Stated another way, aqueous solution is loaded into a pipette tip connected to a pipette (such as a manual or electric air-displacement micropipette). The pipette tip is inserted into an inlet of an example of the microfluidic droplet generator disclosed herein. Pressure is applied using the pipette to expel the aqueous solution from the pipette tip through the inlet and microchannel and into the sample reservoir. The sample reservoir contains reservoir fluid that is immiscible in water. As the aqueous solution flows through the microchannel and into the reservoir fluid contained in the sample reservoir, a step gradient in height at the reservoir end of the microchannel intersecting the sidewall of the sample reservoir causes step-emulsification of the aqueous solution into monodisperse droplets.

Figure 2:
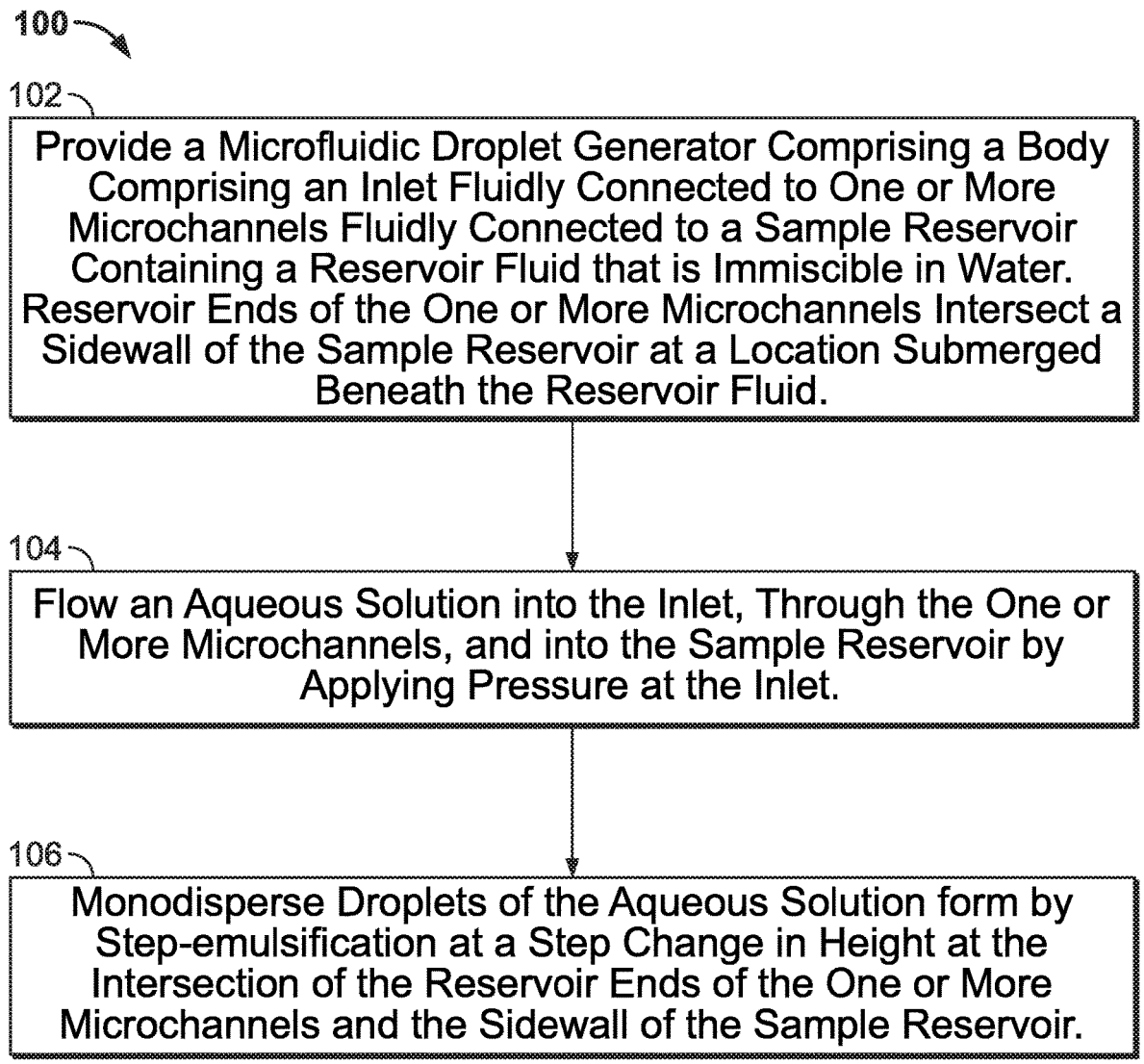
FIG. 2 is a flow diagram illustrating an example of the disclosed method for producing monodisperse aqueous droplets.

FIG. 2 provides a flow diagram illustrating an implementation 100 of an example of the disclosed method of producing aqueous droplets. In the illustrated implementation, at step 102, a microfluidic droplet generator is provided that comprises a body comprising an inlet fluidly connected to one or more microchannels fluidly connected to a sample reservoir containing a reservoir fluid that is immiscible in water. The reservoir ends of the one or more microchannels intersect a sidewall of the sample reservoir at a location submerged beneath the reservoir fluid. At step 104, an aqueous solution is flowed into the inlet, through the one or more microchannels, and into the sample reservoir by applying pressure at the inlet. The pressure can be applied at the inlet by any suitable means, for example by a pipette inserted at the inlet as depicted in FIG. 1. At step 106, monodisperse droplets of the aqueous solution form by step-emulsification at a step change in height at the intersection of the reservoir ends of the one or more microchannels and the sidewall of the sample reservoir as the aqueous solution flows from the one or more microchannels into the sample reservoir. The monodisperse droplets of the aqueous solution are subsequently collected and processed as needed for further use.

An advantage of the method provided herein is that the shape and size of the one or more microchannels in the microfluidic droplet generator is configured to provide sufficient fluidic resistance to the flow of the aqueous solution (such as a hydrogel precursor solution) to limit flow velocity to "dripping" but not "jetting" of droplets at the sample reservoir end of the microchannel over a varying range of pressure, including the range of pressure provided by a manual or electronic air-displacement pipette. Dripping conditions are preferred to provide for monodisperse droplet formation. Accordingly, in several examples, flow of the aqueous solution (such as a hydrogel precursor solution) through the microfluidic droplet generator is driven by a manual or electronic air-displacement micropipette and droplets of the aqueous solution form by dripping at the sample reservoir end of the microchannel.

The applied pressure forces the aqueous solution (such as a hydrogel precursor solution) through the microchannel of the microfluidic droplet generator at a suitable flow rate for formation of the monodisperse aqueous droplets. In addition to the geometry of the microchannel, the flow rate of the aqueous solution through the microchannel may also affect the size and uniformity of the resulting monodisperse droplets. In some examples, the flow rate of the aqueous solution (such as a hydrogel precursor solution) at the outlet end of the microchannel is from about 0.5 µL/min to about 100 µL/min, such as from about 0.5 µL/min to about 100 µL/min, for example, about 0.5, about 1, about 2, about 3, about 4, or about 5 µL/min.

In some examples, the aqueous solution is less dense than the corresponding reservoir fluid. This creates a buoyancy force on droplets of the aqueous solution forming at the step gradient in height at the intersection of the microchannel and sample reservoir that promotes step-emulsification of the droplets and also clearance of the droplets from the reservoir end of the microchannel.

In some examples, genetic material (such as genomic DNA or single cells or cell lysate) is included in the aqueous solution to produce monodisperse aqueous droplets that encapsulate the genetic material. Non-limiting examples of genetic material that can be encapsulated within the aqueous solution include DNA, such as genomic or cDNA; RNA, such as mRNA, sRNA or rRNA; or a hybrid of DNA and RNA.

In some examples, the disclosed method is used to produce hydrogel beads. In such examples, a hydrogel precursor solution is used as the aqueous solution. The hydrogel precursor solution (the disperse phase) is loaded into the microfluidic droplet generator at the inlet, flows through the microchannel, and exits into the sample reservoir containing the reservoir fluid that is immiscible in water (the continuous phase). Monodisperse droplets of the hydrogel precursor solution form by step emulsification at the height change in the microchannel where it intersects the sidewall of the sample reservoir. The monodisperse droplets of the hydrogel precursor solution are incubated under conditions suitable for gelation to form the hydrogel beads.

As used herein, a "hydrogel precursor solution" is an aqueous solution comprising components of a hydrogel (such as hydrogel polymer and crosslinker) but in some examples undergo a pre-selected treatment to initiate gelation. In some examples, the hydrogel precursor solution contains all the components for forming a hydrogel, including hydrogel polymer and crosslinker, except a gelation catalyst for the hydrogel polymer and crosslinker. In such examples, the pre-selected treatment is incubation with the gelation catalyst to initial gelation of the hydrogel. In some examples, the hydrogel precursor solution contains all the components for forming a hydrogel and is kept at a temperature that maintains a solution state. In such examples, the pre-selected treatment is changing the temperature to a gelation temperature to initial gelation of the hydrogel.

As used herein, "hydrogel bead" refers to a population of distinct (not aggregated) microscale colloid gels formed from organic polymer (natural or synthetic) that is crosslinked via covalent, ionic, or hydrogen bonds to create a three-dimensional open-lattice structure that entraps water molecules. Hydrogel beads in some examples are at least substantially spherical in shape, although other shapes are also possible.

Figure 3:
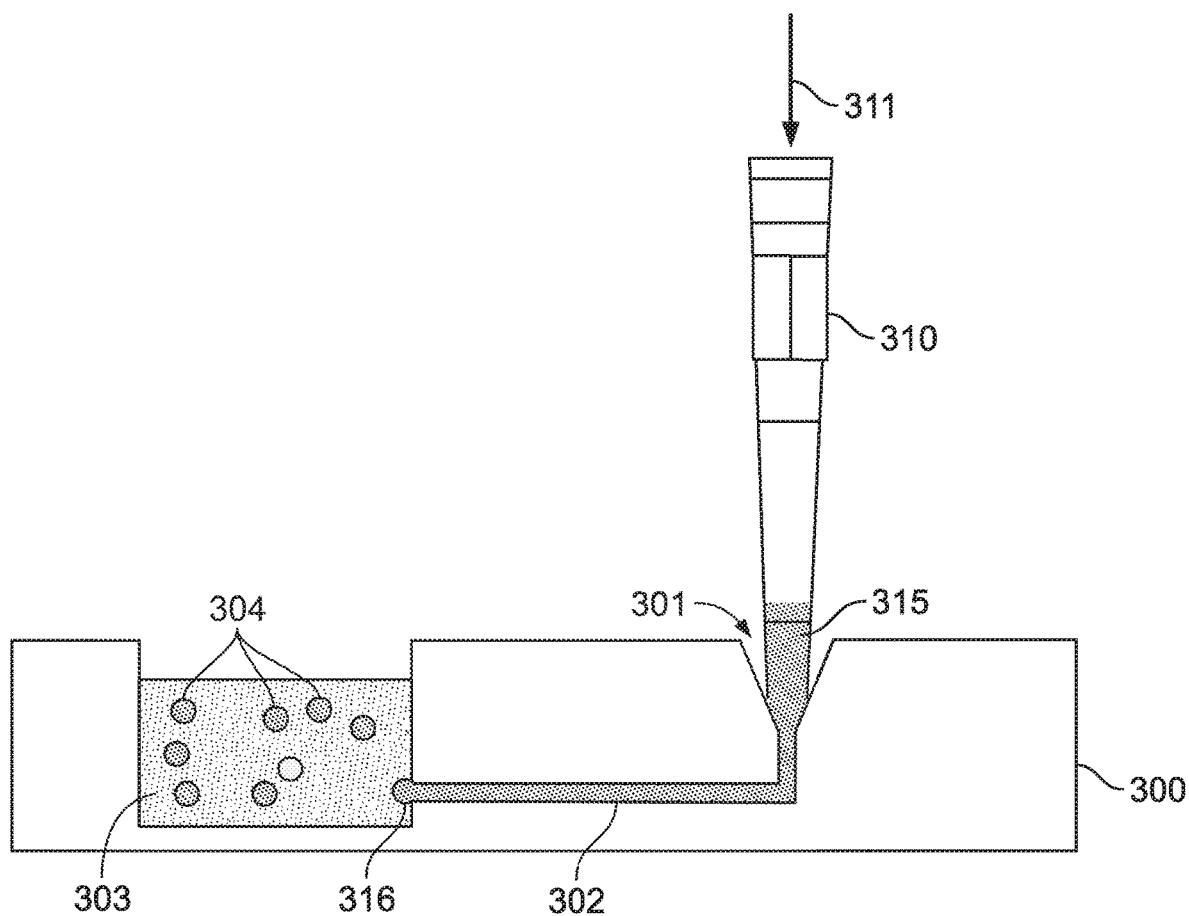
FIG. 3 is a schematic illustration of an example of the disclosed method for producing aqueous droplets, wherein the method further comprises producing hydrogel beads.

FIG. 3 is a schematic illustration of an example of the disclosed method for producing aqueous droplets, wherein the method further comprises producing hydrogel beads. As depicted, hydrogel precursor solution is loaded into a pipette tip, which is inserted into an inlet of a microfluidic droplet generator as disclosed herein. In this example, the hydrogel precursor solution contains components for forming a hydrogel but does not include a gelation catalyst. Pressure is applied to the hydrogel precursor solution in the pipette tip using a manual or electric micropipette connected to the pipette tip to induce flow of the hydrogel precursor solution through the inlet and microchannel and into a sample reservoir. The sample reservoir contains reservoir fluid that is immiscible in water and contains a gelation catalyst that triggers gelation of the hydrogel precursor solution. Monodisperse droplets of the hydrogel precursor solution form by step emulsification at the intersection of the reservoir end of the microchannel and the sample reservoir. In the sample reservoir, the monodisperse droplets of the hydrogel precursor solution contact the gelation catalyst and undergo gelation to form the hydrogel beads.

An implementation of the disclosed method wherein the method is used to prepare hydrogel beads is depicted in FIG. 3. In this implementation, the aqueous solution is a hydrogel precursor solution that contains all the components necessary for forming a hydrogel except a gelation catalyst. The hydrogel precursor solution 315 is loaded into a pipette tip 310 connected to a pipette (such as a manual or electric air-displacement micropipette). The pipette tip 310 is inserted into an inlet 301 of an example of the microfluidic droplet generator 300 disclosed herein. Pressure 311 is applied using the pipette to expel the hydrogel precursor solution from the pipette tip 310 through the inlet 301 and microchannel 302 and into the sample reservoir. The sample reservoir contains reservoir fluid 303 that is immiscible in water and comprises a gelation catalyst. As the solution flows through the microchannel 302 and into the reservoir fluid 303 contained in the sample reservoir, a step gradient in height at the reservoir end of the microchannel intersecting the sidewall of the sample reservoir causes step-emulsification of the hydrogel precursor solution 316 into monodisperse droplets. The monodisperse droplets of the hydrogel precursor solution undergo gelation in the presence of the gelation catalyst in the sample reservoir to form the hydrogel beads 314.

Figure 4:
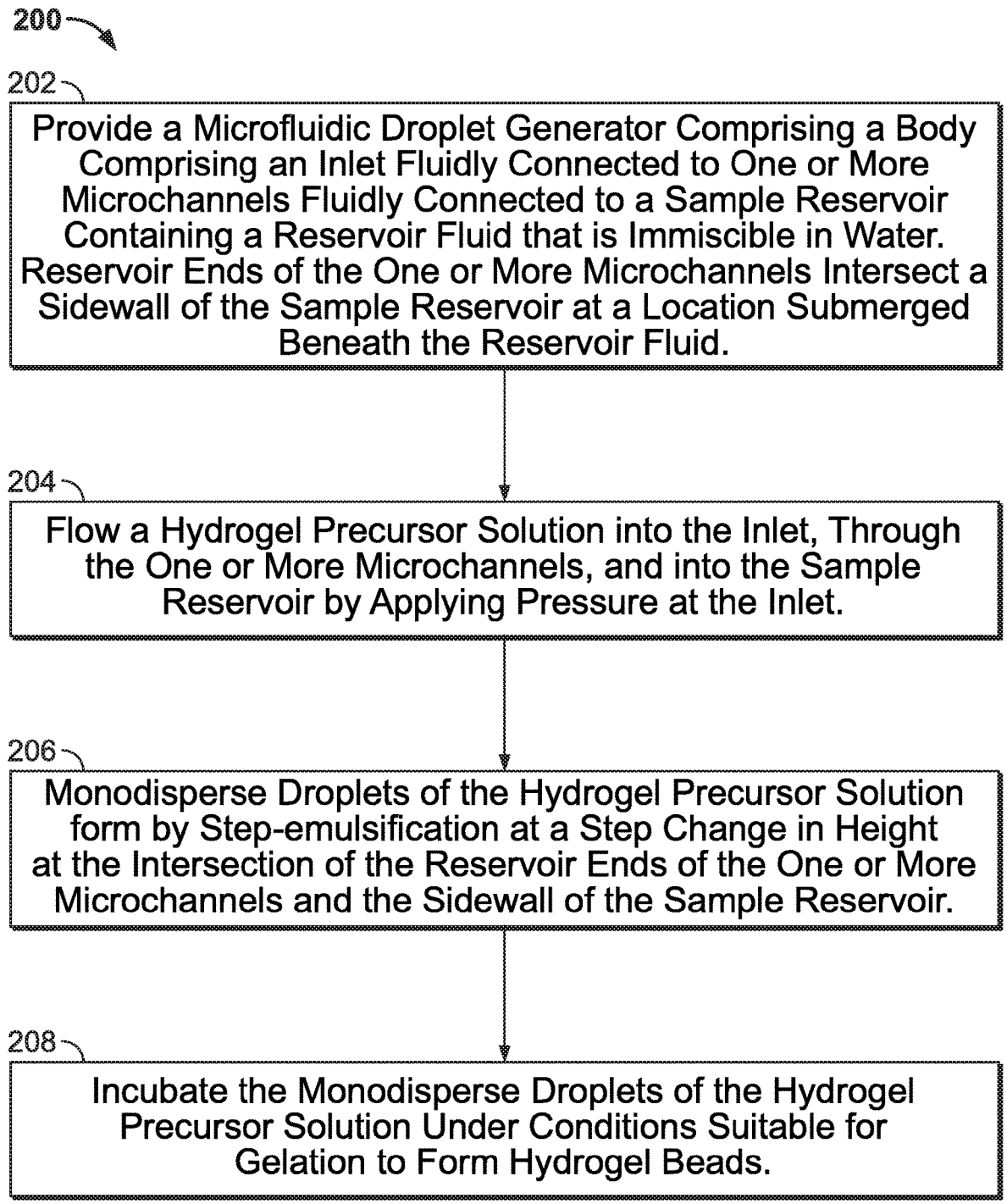
FIG. 4 is a flow diagram illustrating an example of the disclosed method for producing aqueous droplets, wherein the method further comprises producing hydrogel beads.

FIG. 4 provides a flow diagram illustrating an implementation 200 of an example of the disclosed method, wherein the method is used to produce hydrogel beads. In the illustrated implementation, at step 202, a microfluidic droplet generator is provided that comprises a body comprising an inlet fluidly connected to one or more microchannels fluidly connected to a sample reservoir containing a reservoir fluid that is immiscible in water. The reservoir ends of the one or more microchannels intersect a sidewall of the sample reservoir at a location submerged beneath the reservoir fluid. At step 204, a hydrogel precursor solution is flowed into the inlet, through the one or more microchannels, and into the sample reservoir by applying pressure at the inlet. The pressure can be applied at the inlet by any suitable means, for example by a pipette inserted at the inlet as depicted in FIG. 3. At step 206, monodisperse droplets of the hydrogel precursor solution form by step-emulsification at a step change in height at the intersection of the reservoir ends of the one or more microchannels and the sidewall of the sample reservoir as the hydrogel precursor solution flows from the microchannel into the sample reservoir. At step 208, the monodisperse droplets of the hydrogel precursor solution are incubated under conditions suitable for gelation to form hydrogel beads. For example, in implementations where the hydrogel precursor solution contains all the components necessary for forming a hydrogel except a gelation catalyst, the monodisperse droplets can be contacted with the gelation catalyst to initiate gelation of the droplets to form the hydrogel beads. Any suitable method can be used to contact the monodisperse droplets of the hydrogel precursor with the gelation catalyst. In some examples, the gelation catalyst is included in the reservoir fluid and the monodisperse droplets of the hydrogel precursor contact the gelation catalyst upon formation in the reservoir fluid. In another example, the reservoir fluid containing the monodisperse droplets of the hydrogel precursor is collected from the sample reservoir and transferred to a container, and the gelation catalyst is added to the container to induce gelation of the hydrogel beads.

After the hydrogel beads are produced, they can be further processed for downstream use, for example by washing in aqueous solution to remove excess hydrogel crosslinker and any reservoir fluid. Once produced, the hydrogel beads can be used for any suitable purpose, such as in sequencing procedures. In some examples, the hydrogel beads produced using the disclosed method are subsequently functionalized to contain immobilized transposoms on the bead surface (e.g., as described in the U.S. Pat. Pub. Nos. 2014/0194324 or 2018/0155709, which are incorporated by reference herein). The transposome-modified beads can be used, for example, in bead-linked tagmentation (BLT) assays for sequencing procedures. Linkage of transposomes to the bead surface can be accomplished using any suitable method, for example by functionalizing the bead surface with a first member of a specific binding pair and then capturing transposomes linked to the second member of the specific binding pair. In some examples, the bead and bead surface are functionalized with avidin (or an analogue thereof, such as streptavidin) and biotinylated transposomes are captured on the functionalized bead surface.

Additional features and implementation of the disclosed method and microfluidic droplet generator are described in more detail below.

Microfluidic Droplet Generator

Implementations of the method provided herein utilize a microfluidic droplet generator to form monodisperse aqueous droplets (such as monodisperse droplets of hydrogel precursor solution) by step emulsification.

As used herein, the term "microfluidic droplet generator" refers to a device that incorporates at least one microchannel that has at least one cross sectional dimension in the range of from about 0.1 μm to about 500 μm, such as from about 1 μm to about 100 μm, and which can be used to generate aqueous droplets by step emulsification, where the droplets have a diameter of from about 1 μm to about 200 μm. A "microchannel" is a microchannel in a microfluidic device that has at least one micro-scale cross-sectional dimension, such as a dimension of from 1-200 μm.

The microfluidic droplet generator comprises a body structure in which the various microfluidic elements are disposed. In some implementations, the body structure has a single inlet fluidly connected to one or more microchannels each fluidly connected to a sample reservoir. The microchannels each comprises a reservoir end and an inlet end. The inlet end of the microchannel is fluidly connected to the inlet. The reservoir end of the microchannel intersects a sidewall of the sample reservoir at an angle substantially perpendicular to the ground. In implementations of the disclosed method, the sample reservoir contains a reservoir fluid and the reservoir end of the microchannel is submerged beneath the reservoir fluid.

The body structure of the microfluidic droplet generator typically employs a solid or semi-solid substrate that is planar in structure, for example, at least substantially flat or having at least one flat surface, and defines the various microscale channels and other elements of the microfluidic droplet generator. Suitable substrates may be fabricated from any one of a variety of materials, or combinations of materials. Often, the planar substrates are manufactured using solid substrates common in the fields of microfabrication, for example, silicon, polysilicon, and silica-based substrates, such as glass and quartz, as well as other known substrates, for example, gallium arsenide. In the case of these substrates, common microfabrication techniques, such as photolithographic techniques, wet chemical etching, micromachining, for example, drilling, milling and the like, may be readily applied in the fabrication of microfluidic devices and substrates. Alternatively, polymeric substrate materials may be used to fabricate the microfluidic droplet generator, including, e.g., polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, ABS (acrylonitrile-butadiene-styrene copolymer), cyclic olefin copolymer (COC), cyclo olefin polymer (COP), and the like. In the case of such polymeric materials, injection molding or embossing methods may be used to form the substrates having the microchannel and reservoir geometries as described herein. In some cases, original molds may be fabricated using any of the above described materials and methods.

The microfluidic droplet generator can be any suitable size for use in the method provided herein.

In some examples, the inlet, one or more microchannels, and reservoir of the microfluidic droplet generator are fabricated into one surface of a planar substrate, as grooves, wells, passages, or depressions in that surface. A second planar substrate, in some examples prepared from the same or similar material, is overlaid and bonded to the first, thereby defining and sealing the channels and/or chambers of the microfluidic droplet generator. Together, the upper surface of the first substrate, and the lower mated surface of the upper substrate, define an interior portion of the microfluidic droplet generator, for example, defining the channels and chambers of the microfluidic droplet generator.

Figure 5:
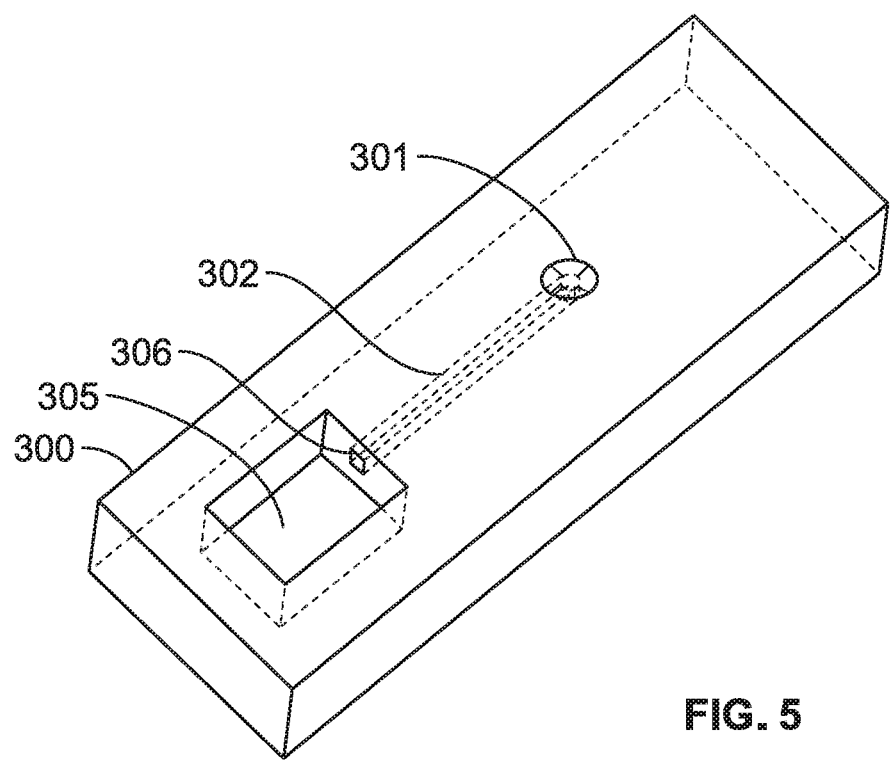
FIG. 5 is an illustration of a perspective view of a microfluidic droplet generator as provided herein.

An example of a microfluidic droplet generator for use in the disclosed method is shown in FIG. 5. As shown, the microfluidic droplet generator 300 includes a body, containing an inlet 301 fluidly connected to a microchannel 302 that runs longitudinally down the central portion of the body to a sample reservoir 305. The microchannel 302 comprises an inlet end that is in fluid communication with the inlet 301 and terminates at the reservoir end 306 and is in fluid communication with the sample reservoir 305.

Stated another way, as depicted, an inlet is located on an upper surface of the body of the microfluidic droplet generator, and is fluidly connected to a microchannel that travels horizontally to the ground and longitudinally through the body of the microfluidic droplet generator and intersects with a sample reservoir at the reservoir end of the microchannel. Like the inlet, the sample reservoir is open to the upper surface of the body of the microfluidic droplet generator.

Figure 6:
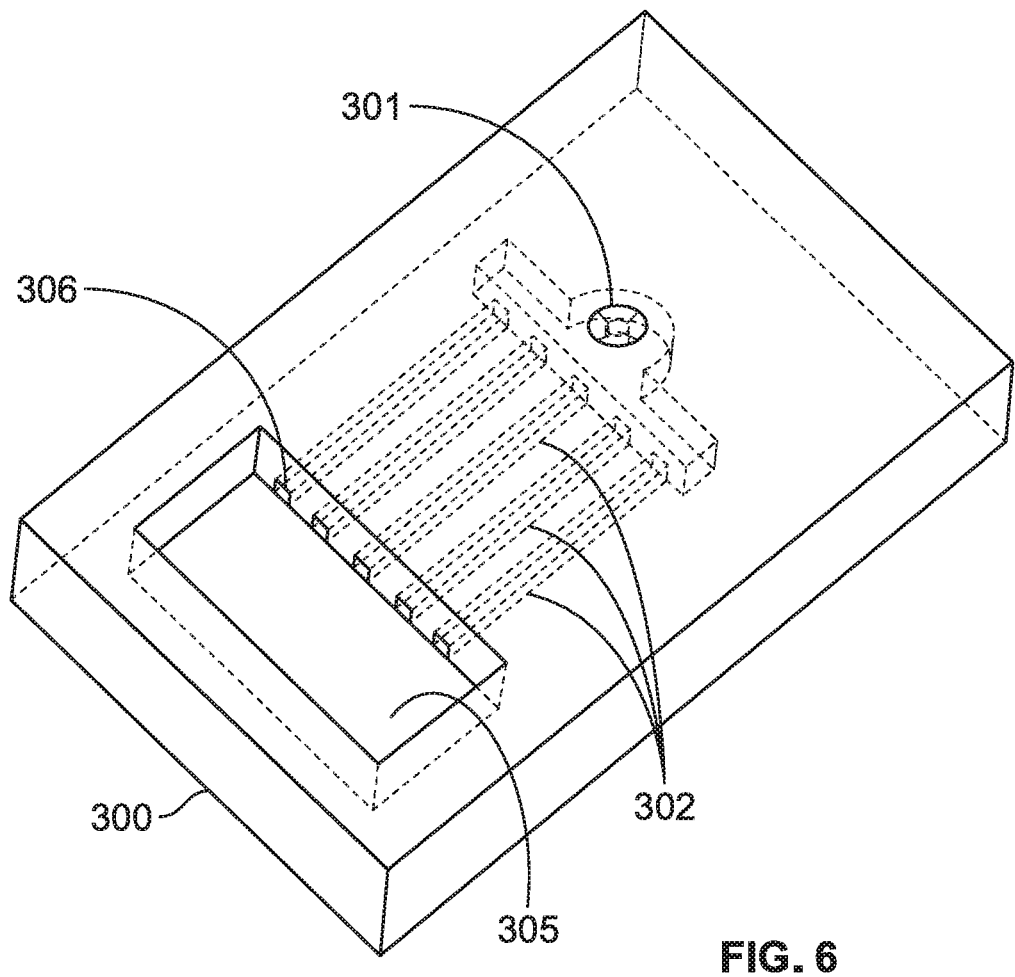
FIG. 6 is an illustration of a perspective view of a microfluidic droplet generator as provided herein.

Another example of a microfluidic droplet generator for use in the disclosed method is shown in FIG. 6. As depicted, an inlet 301 is located on an upper surface of the body of the microfluidic droplet generator 300, and is fluidly connected to five microchannels 302 via a chamber. The microchannels 302 travel horizontally to the ground and longitudinally through the body of the microfluidic droplet generator 300 and intersect with a sample reservoir 305 at the reservoir end 306 of the microchannels 302. Like the inlet 301, the sample reservoir 305 is open to the upper surface of the body of the microfluidic droplet generator 300.

As shown in FIG. 6, the microfluidic droplet generator includes a body, containing an inlet fluidly connected to multiple microchannels via a chamber. The multiple microchannels run longitudinally down the central portion of the body to a sample reservoir. The microchannels comprise inlet ends that are in fluid communication with the inlet via the chamber and terminate at sample reservoir ends that are in fluid communication with the sample reservoir. FIG. 6 depicts a microfluidic droplet generator with five microchannels. However, the microfluidic droplet generator for use with the disclosed method can have any suitable number of microchannels. In some examples, the microfluidic droplet generator has from 1-10 microchannels (such as 1, 2, 3, 4, 5, 6, 7, 8, 9, or 10 microchannels).

The inlet of the microfluidic droplet generator in some examples is located on an upper surface of the body structure and is fluidly connected to the microchannel of the microfluidic droplet generator. The inlet can have any suitable shape for mating with a vessel (such as a pipette tip or tube) for loading the aqueous solution into the microfluidic droplet generator. In some examples, the inlet is a recess in the upper surface of the upper surface of the body structure and is fluidly connected to the microchannel of the microfluidic droplet generator.

Figure 7:
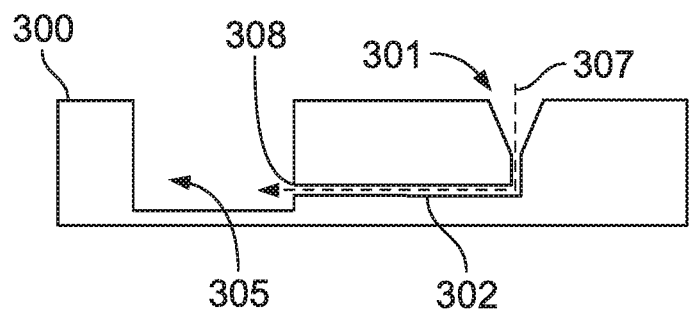
FIG. 7 is an illustration of a cross-sectional view of the microfluidic droplet generator shown in FIG. 5. The direction of flow through the microfluidic droplet generator is shown.

With reference to FIG. 7, in some examples, the inlet 301 has an inverted conical shape, with the apex of the conical shape fluidly connected to the microchannel 302 and the opposite end of the cone open to the upper surface of the body of the microfluidic droplet generator 300. A pipette tip can be inserted into the inverted conical shape of the inlet to form a seal (see, for example, FIGS. 8-11). In several examples, the seal is an air-tight seal, which allows air pressure applied with an appropriate device (such as a micropipette or a pump (for example, a pneumatic pump), or a syringe) attached to the pipette tip to drive flow 307 of the aqueous solution through the inlet and microchannel to a step gradient 308 in height at reservoir end of microchannel, and into the sample reservoir 305 (for example, as depicted in FIG. 1).

Figure 8:
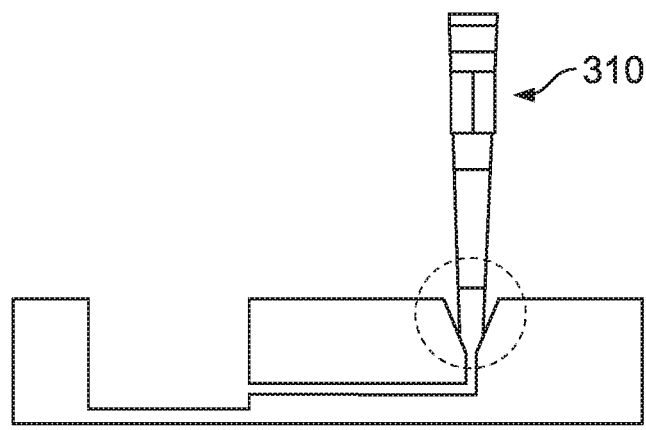
FIG. 8 is an illustration of a cross-sectional view of the microfluidic droplet generator shown in FIG. 5.

FIG. 8 is an illustration of a cross-sectional view of the microfluidic droplet generator shown in FIG. 5. As depicted, a pipette tip 310 is inserted into the inlet of the microfluidic droplet generator. In this example, the inlet has an inverted conical shape that mates with the pipette tip to facilitate loading of the aqueous solution into the microfluidic droplet generator.

Figure 9:
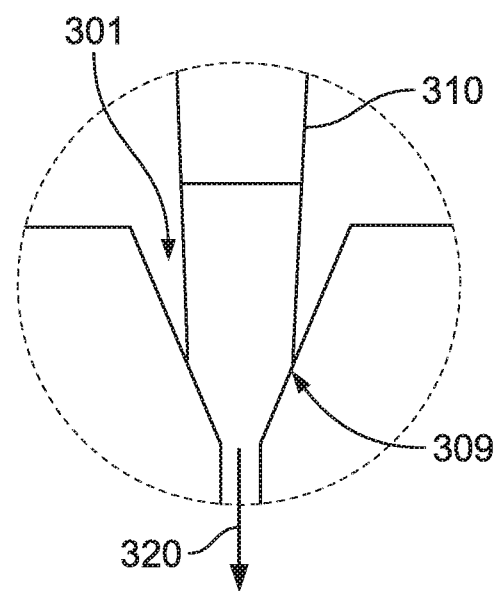
FIG. 9 is an illustration of an expanded view of the area circled in FIG. 8. As depicted, the edge of the pipette tip contacts the surface of the inlet to form a tight seal.

FIG. 9 is an illustration of an expanded view of the area circled in FIG. 8. As depicted, the edge of the pipette tip 310 contacts the surface of the inlet to form a tight seal 309.

Figure 10:
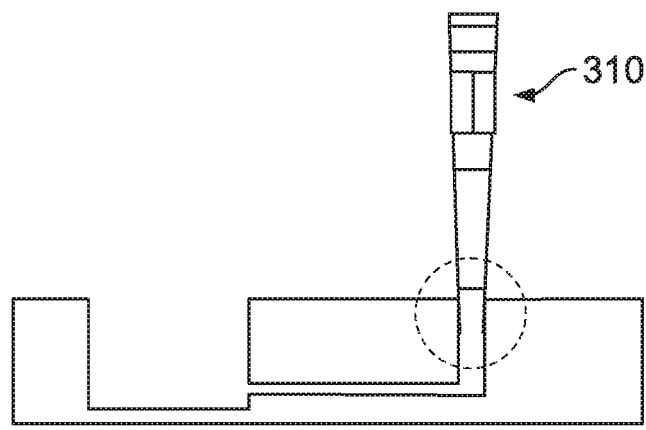
FIG. 10 is an illustration of a cross-sectional view of a microfluidic droplet generator designed for use with the method of producing monodisperse aqueous droplets described herein.
Figure 11:
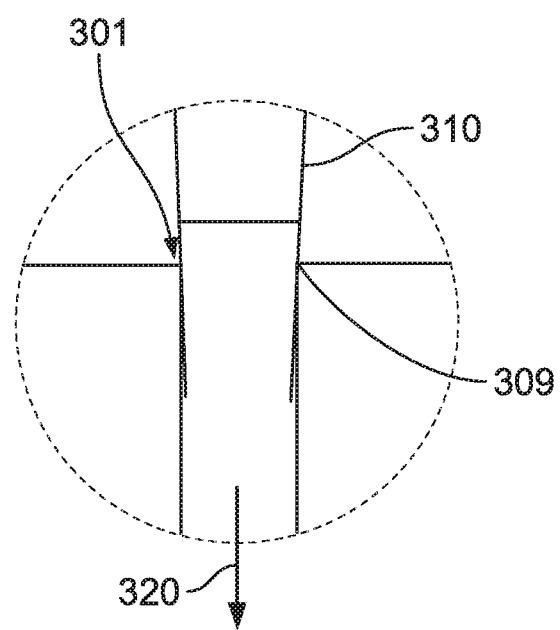
FIG. 11 is an illustration of an expanded view of the area circled in FIG. 10. As depicted, the outer surface of the pipette tip contacts the upper lip of the inlet to form a tight seal.

With reference to FIG. 10, in some examples, the inlet has a tubular shape, with one end of the tube fluidly connected to the microchannel and the opposite end of the tube open to the upper surface of the body of the microfluidic droplet generator. The microfluidic droplet generator is similar to the microfluidic droplet generator depicted in FIG. 5, but with a tubular-shaped inlet. As depicted, a pipette tip 310 is inserted into the inlet of the microfluidic droplet generator to facilitate loading of the aqueous solution into the microfluidic droplet generator. A pipette tip 310 can be inserted into the tubular shape of the inlet 301 to form a seal 309 (see, for example, FIG. 11). In several examples, the seal 309 is an air-tight seal, which allows air pressure applied with an appropriate device (such as a micropipette or a pump or a syringe) attached to the pipette tip to drive flow 320 of the aqueous solution through the inlet and microchannel and into the sample reservoir (for example, as depicted in FIG. 1).

Figure 12:
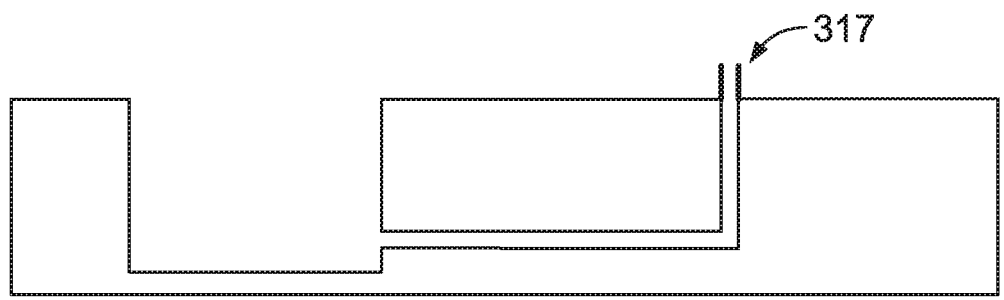
FIG. 12 is an illustration of a cross-sectional view of a microfluidic droplet generator designed for use with the method provided herein.
Figure 13:
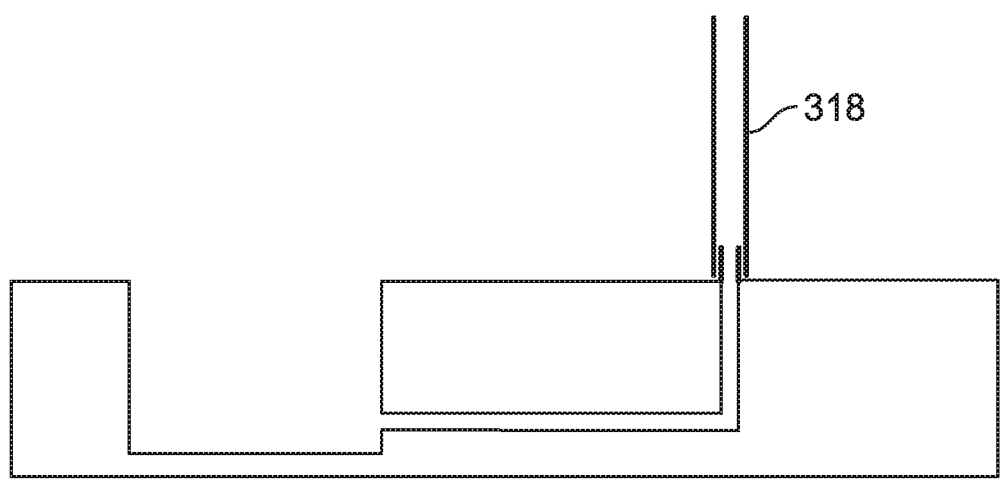
FIG. 13 is an illustration of a cross-sectional view of the microfluidic droplet generator shown in FIG. 12, depicted with a tube connected to the nozzle-shaped inlet.

In another example, the inlet is raised from the upper surface of the body structure and has a nozzle shape that can mate with a suitably shaped vessel containing the aqueous solution, such as a tubular vessel. FIG. 12 depicts an example of a microfluidic droplet generator with a nozzle-shaped inlet 317 raised from the upper surface of the body structure. The microfluidic droplet generator is similar to the microfluidic droplet generator depicted in FIG. 5, but with a nozzle-shaped inlet. FIG. 13 shows the microfluidic droplet generator with a tube 318 connected to the nozzle-shaped inlet. Mounting the tube on the nozzle-shaped inlet forms a seal. In several examples, the seal is an air-tight seal, which allows air pressure applied with an appropriate device (such as a micropipette or a pump or a syringe) attached to the tube to drive flow of aqueous solution through the inlet and microchannel and into the sample reservoir.

Figure 14:
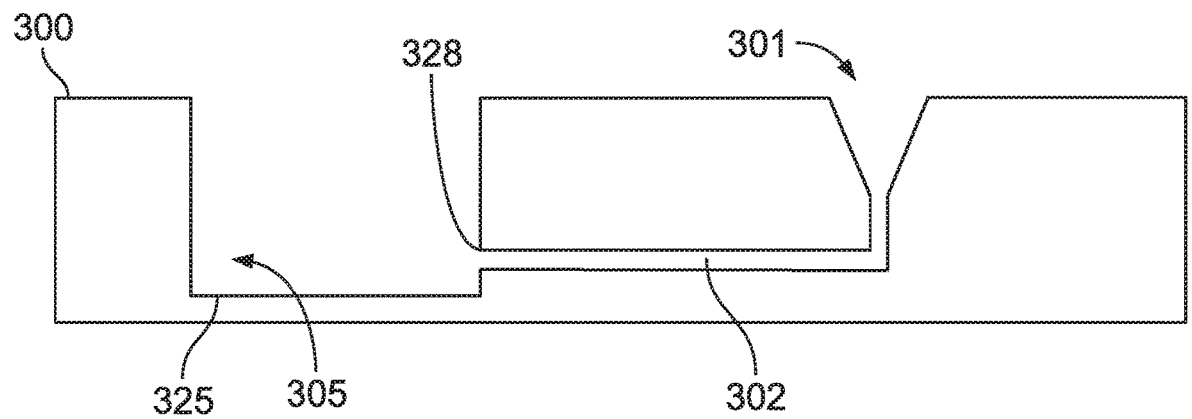
FIG. 14 is an illustration of a cross-sectional view of a microfluidic droplet generator designed for use with the method provided herein.

FIG. 14 is an illustration of a cross-sectional view of a microfluidic droplet generator designed for use with the method provided herein. The microfluidic droplet generator 300 is similar to the microfluidic droplet generator depicted in FIG. 5, but with a microchannel 302 that intersects the sidewall of the sample reservoir 305 at a location 328 adjacent to the floor 325 of the sample reservoir 305, creating a step gradient in height.

The microchannel of the microfluidic droplet generator can have any suitable shape for use in the method provided herein. In some examples, the microchannel can have a varying shape. For example, the microchannel can have a greater cross-sectional area at the inlet end than at the reservoir end.

As discussed above, an advantage of the method provided herein is that the shape and size of the one or more microchannels in the microfluidic droplet generator is configured to provide sufficient fluidic resistance to the flow of the aqueous solution (such as hydrogel precursor solution) to limit flow velocity to "dripping" but not "jetting" of droplets over a varying range of pressure, including the range of pressure provided by a manual or electronic air-displacement pipette.

Any suitable amount of pressure can be applied at the inlet to force the aqueous solution (such as hydrogel precursor solution) through the microfluidic droplet generator. In several examples, flow of the aqueous solution through the microfluidic droplet generator is driven by a manual or electronic air-displacement micropipette. In some examples, the pressure at the inlet is constant or varying pressure of up to about 2000 Pa.

In a non-limiting example, the shapes of the inlet and microchannel are configured to provide a hydrodynamic resistance to water of from about $5 \times 10^{13}$ L/m$^3$ to about $5 \times 10^{14}$ L/m$^3$. In some examples, the shapes of the inlet and microchannel are configured to provide a hydrodynamic resistance to water that limits the flow rate through the microchannel to from about 0.5 μL/min to about 5 μL/min over a varying range of pressure, including the range of pressure provided by a manual or electronic air-displacement pipette.

The one or more microchannels of the microfluidic droplet generator can have any suitable length for use in the method provided herein. In some examples, the length of the microchannel is at least 100 μM, such as 300 μm. In some examples, the length of the microchannel is from about 100 μm to about 5 mm, such as from about 1 mm to about 3 mm.

In some examples, the one or more microchannels have a cross-sectional height of about 5 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, or a cross-sectional height within a range defined by any two of the aforementioned values. In some examples, the one or more microchannels have a cross-sectional width of about 5 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, or a cross-sectional width within a range defined by any two of the aforementioned values. In some examples, the one or more microchannels have a round or oval shaped cross-sectional area. For example, in some examples, the one or more microchannels have a cross sectional diameter of about 5 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, or a cross-sectional diameter within a range defined by any two of the aforementioned values. Other width values are possible as the cross-sectional area can vary to finely tune the size of the resulting monodisperse aqueous droplets.

The cross-sectional area of the reservoir ends of the one or more microchannels correlates with the size of the monodisperse aqueous droplets formed by step emulsification as the aqueous solution flows from the microchannel and into the sample reservoir. A smaller cross-sectional area of the reservoir ends of the one or more microchannels leads to formation of smaller aqueous droplets.

The reservoir ends of the one or more microchannels can have any shape that facilitates step-emulsification of the aqueous solution as it flows from the microchannel into the sample reservoir. In some examples, the reservoir ends of the one or more microchannels have a rectangular shape (for example, as depicted in FIG. 5). In other examples, the reservoir ends of the one or more microchannels have a square, circular, or oval shape.

In some examples, the reservoir ends of the one or more microchannels have a cross-sectional height of about 5 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, or a cross-sectional height within a range defined by any two of the aforementioned values. In some examples, the reservoir ends of the one or more microchannels have a cross-sectional width of about 5 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, or a cross-sectional width within a range defined by any two of the aforementioned values. In some examples, the reservoir ends of the one or more microchannels have a round or oval shaped cross-sectional area. For example, in some examples, the reservoir ends of the one or more microchannels have a cross sectional diameter of about 5 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, or about 200 μm, or a cross-sectional diameter within a range defined by any two of the aforementioned values. Other width values are possible as the cross-sectional area can vary to finely tune the size of the resulting aqueous droplets.

The reservoir ends of the one or more microchannels can intersect the sidewall of the sample reservoir at any location that facilitates step-emulsification of the aqueous solution as it flows from the one or more microchannels into the sample reservoir. In some examples, the reservoir ends of the one or more microchannels intersect the sidewall of the sample reservoir at a location that is above the floor of the sample reservoir and below the top of the reservoir sidewall (for example, as depicted in FIGS. 5 and 7). In another example, the reservoir ends of the one or more microchannels intersect the sidewall of the sample reservoir adjacent to the sample reservoir floor (for example, as depicted in FIGS. 6 and 14).

The reservoir ends of the one or more microchannels typically intersect the sidewall of the sample reservoir at an angle that is perpendicular to the sidewall and parallel to the ground. However, additional geometries may also be used. In some examples, the reservoir ends of the one or more microchannels intersect the sidewall of the sample reservoir at an angle that is ±10 degrees from perpendicular to the sidewall and ±10 degrees from parallel to the ground. In some examples, the reservoir ends of the one or more microchannels intersects the sidewall of the sample reservoir at an angle that is ±5 degrees from perpendicular to the sidewall and ±5 degrees from parallel to the ground.

The shape and positioning of the reservoir ends of the one or more microchannels allow for both buoyancy and shear stress on the aqueous solution as it exits the one or more microchannels and contacts the reservoir fluid in the sample reservoir, which leads to droplet formation by step emulsification as the aqueous solution flows into the sample reservoir.

Figure 15:
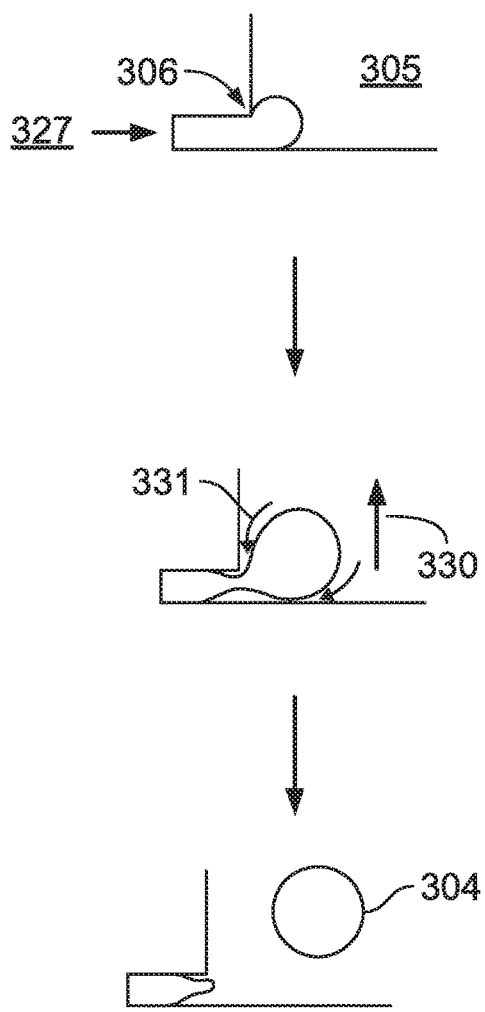
FIG. 15 is a schematic diagram illustrating microfluidic droplet formation by step emulsification as the aqueous solution flows from the reservoir end of the microchannel and into the reservoir fluid contained in the sample reservoir.

FIG. 15 is a schematic diagram illustrating microfluidic droplet formation by step emulsification as the aqueous solution flows 327 from the reservoir end of the microchannel and into the reservoir fluid contained in the sample reservoir. A step change in height is located at the reservoir end of the microchannel 302 where the microchannel intersects the sample reservoir 305. The movement of the reservoir fluid (indicated by the curved arrows 331) and the buoyancy force 330 (perpendicular to the direction of flow of the aqueous solution and towards the upper surface of the microfluidic droplet generator) provide sheer stress that "pinches" off the droplet 304 from the flow of the aqueous solution as it passes the step change in height. In the illustrated example, the buoyancy force on the droplet is towards the upper surface of the microfluidic droplet generator because the aqueous solution is less dense than the reservoir fluid contained in the sample reservoir.

The step change in height where the one or more microchannels intersect the sample reservoir leads to production of droplets in the reservoir fluid contained in the sample reservoir. As illustrated in FIG. 15, stresses on the forming droplet cause it to separate from the flow stream of aqueous solution. The flow direction of the reservoir fluid (indicated by the curved arrows) and the buoyancy force (perpendicular to the direction of flow of the aqueous solution in the illustrated example) provide sheer stress that "pinches" off the droplet from the flow of the aqueous solution.

In some examples, the length and overall shape of the one or more microchannels are configured to provide sufficient fluidic resistance to limit flow velocity of the aqueous solution to allow "dripping" but not "jetting" of droplets into the sample reservoir within the range of pressure provided by a manual or electronic micropipette. Dripping conditions are preferred to provide for monodisperse droplet formation. In a non-limiting example, the shape of the one or more microchannels is configured to provide a hydrodynamic resistance to water in each microchannel of from about $5 \times 10^{13}$ L/m$^3$ to about $5 \times 10^{14}$ L/m$^3$. In some examples, the shape of the one or more microchannels is configured to provide a hydrodynamic resistance to water that limits the flow rate through each microchannel to from about 0.5 μL/min to about 5 μL/min when a constant or varying pressure of up to about 2000 Pa is applied to the aqueous solution at the inlet of the microfluidic droplet generator.

The sample reservoir of the microfluidic droplet generator can have any shape suitable for use with the method provided herein. As discussed above, the sample reservoir has a floor and sidewall(s) that contain the reservoir fluid, and the one or more microchannels of the microfluidic droplet generator intersect a sidewall of the sample reservoir. In some examples, the upper portion of the sample reservoir is open to the air (e.g., has no cover), although other configurations are also possible, such as a sample reservoir with a removable cover.

In some examples, a microfluidic droplet generator is provided that comprises the elements of the microfluidic droplet generator for use in the method of producing aqueous droplets provided herein.

Reservoir Fluid

The sample reservoir in the microfluidic droplet contains a fluid (the "reservoir fluid") that is immiscible in water. Any appropriate water-immiscible fluid can be used. In some examples, the reservoir fluid is denser than the aqueous solution. The sample reservoir is filled with the reservoir fluid to at least a level that submerges the reservoir end of the one or more microchannels where they intersect the sidewall of the sample reservoir.

In some examples, the reservoir fluid is a hydrophobic liquid, such as oil, for example, mineral oil or silicone oil, or perfluorinated oil, or a combination of two or more thereof. In other examples, the reservoir fluid is a viscous solution that impedes diffusion of genomic material such as buffers containing polymers such as poly-ethylene glycol (PEG), poly-vinyl-pyrrolidone, pluronic dextran, sucrose, and the like.

In some examples, the reservoir fluid comprises a fluorinated oil, such as 1,1,2,2,3,3,4,4,4-Nonafluoro-N-(nonafluorobutyl)-N-(1,1,2,2-tetrafluoroethyl)-1-butanamine or 3-ethoxyperfluoro(2-methylhexane).

The reservoir fluid typically includes a surfactant to increase droplet segregation. Any appropriate surfactant and amount thereof can be included in the reservoir fluid, such as from 0.5 to 10% surfactant v/v, for example, 1%, 2%, 3%, 4%, 5%, 6%, 7%, 8%, 9%, or 10% surfactant v/v. In some examples, the surfactant is a fluorosurfactant, such as RAN Biotechnologies 008 fluorosurfactant.

In several examples involving production of hydrogel beads, the reservoir fluid contains one or more agents that induce gelation of the monodisperse droplets of the hydrogel precursor solution, such as a gelation catalyst or a gelation initiator, or a gelation initiator and a gelation catalyst. The gelation catalyst and initiator included in the reservoir fluid are selected to induce gelation of the hydrogel precursor solution.

In a non-limiting example, the reservoir fluid comprises or consists of 1,1,2,2,3,3,4,4,4-Nonafluoro-N-(nonafluorobutyl)-N-(1,1,2,2-tetrafluoroethyl)-1-butanamine and a fluorosurfactant (such as RAN Biotechnologies 008 fluorosurfactant). In some such examples, the reservoir fluid further comprises a gelation catalyst, such as tetramethylethylenediamine (TEMED), for example, to induce gelation of an acrylamide-based hydrogel precursor solution.

In another example, the reservoir fluid comprises or consists of 1,1,2,2,3,3,4,4,4-Nonafluoro-N-(nonafluorobutyl)-N-(1,1,2,2-tetrafluoroethyl)-1-butanamine and 3-ethoxyperfluoro(2-methylhexane), and a fluorosurfactant (such as RAN Biotechnologies 008 fluorosurfactant). In some such examples, the reservoir fluid further comprises a gelation catalyst, such as TEMED, for example, to induce gelation of an acrylamide-based hydrogel precursor solution.

In another example, the reservoir fluid comprises or, in one example consists of, 3-ethoxyperfluoro(2-methylhexane), and a fluorosurfactant (such as RAN Biotechnologies 008 fluorosurfactant). In some such examples, the reservoir fluid further comprises a gelation catalyst, such as TEMED, for example, to induce gelation of an acrylamide-based hydrogel precursor solution.

Hydrogel Precursor Solution

Any appropriate hydrogel precursor solution can be used in implementations of the disclosed method that comprise production of hydrogel beads.

The hydrogel precursor solution may be an aqueous solution comprising hydrogel precursor materials (e.g., hydrogel polymer and hydrogel crosslinker) and any appropriate additives (such as buffering agents or genetic material) and undergoes gelation under suitable conditions, such as when contacted with appropriate gelation catalyst or a gelation initiator, or a gelation initiator and a gelation catalyst. A hydrogel is a macromolecular polymer gel constructed of a network of crosslinked polymer chains. Hydrogels can be prepared from natural, synthetic or synthetic/natural hybrid polymers and crosslinkers.

A "hydrogel polymer" refers to a hydrophilic polymer that, when reacted under suitable conditions with an appropriate hydrogel crosslinker and gelation initiator and/or catalyst, undergoes gelation to form a hydrogel. A "hydrogel crosslinker" refers to a molecule that can form a three-dimensional network when reacted under suitable conditions with an appropriate hydrogel polymer leading to gelation of the polymer and hydrogel crosslinker into a hydrogel.

The concentration of polymer and crosslinker in the hydrogel precursor solution can vary depending on the desired characteristics of the resulting hydrogel beads. The type and degree of crosslinking influences many of the polymer network properties, such as swelling properties, elastic modulus and transport of molecules. The strength of hydrogels can be increased by increasing the degree of crosslinking. Any suitable amount of hydrogel polymer and crosslinker can be included in the hydrogel precursor solution as long as the resulting solution forms monodisperse droplets by step-emulsification at the step change in height at the intersection of the microchannel and the sample reservoir sidewall, and the monodisperse droplets subsequently undergo gelation to form hydrogel beads when contacted with a suitable amount of an appropriate gelation initiator and/or catalyst.

Non-limiting examples of polymer and/or crosslinker materials that can be used in the hydrogel precursor solution include, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations or mixtures thereof. Non-limiting examples of combinations of hydrogel polymer and crosslinker that can be included in the hydrogel precursor solution include polyethylene glycol (PEG)-thiol/PEG-acrylate, acrylamide/N,N'-bis(acryloyl)cystamine (BACy), and PEG/polypropylene oxide (PPO).

In some examples, the hydrogel crosslinker forms a disulfide bond with monomers of the polymer precursor in the monodisperse hydrogel precursor solution droplets to induce gelation of the hydrogel beads.

In some examples, the hydrogel crosslinker is a reversible hydrogel crosslinker. In some examples, the reversible hydrogel crosslinker is capable of reversibly crosslinking the hydrogel polymer and is capable of being un-crosslinked in the presence of a cleaver. In some examples, a hydrogel crosslinker can be cleaved by the presence of a reducing agent, by elevated temperature, or by an electric field. In some examples, the reversible hydrogel crosslinker may be N,N'-bis(acryloyl)cystamine, a reversible hydrogel crosslinker for polyacrylamide gels, wherein a disulfide linkage may be cleaved in the presence of a suitable reducing agent. Contacting the hydrogel crosslinker with a reducing agent cleaves the disulfide bonds of the hydrogel crosslinker, breaking down the hydrogel beads. The hydrogel beads degrade, and release the contents, such as DNA libraries retained therein. In some examples, the hydrogel crosslinker is cleaved by increasing the temperature to greater than about 50, about 55, about 60, about 65, about 70, about 75, about 80, about 85, about 90, about 95, or about 100° C. In some examples, the hydrogel crosslinker is cleaved by contacting the hydrogel beads with a reducing agent. In some examples, the reducing agents include phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol, tris(2-carboxyethyl)phosphine (TCEP), tris(hydroxymethyl)phosphine (THP), or P[tris(hydroxymethyl)phosphine] propionic acid (THPP), or a combination of two or more thereof. In some examples, the hydrogel crosslinker may be N,N'-(1,2-Dihydroxyethylene) bisacrylamide, a reversible hydrogel crosslinker for polyacrylamide gels, wherein a 1,2-diol linkage may be cleaved in the presence of an oxidation agent such as sodium periodate, and the amidomethylol linkage can be cleaved in the presence of a strong acid such as periodic acid, or a strong base such sodium hydroxide to degrade the bead. In some examples, the hydrogel crosslinker is cleaved by increasing the temperature to greater than about 80, about 85, about 90, about 95, or about 100° C.

In examples where the hydrogel matrix of the bead contains a reversible hydrogel crosslinker, the matrix can be degraded by un-crosslinking the matrix with an appropriate cleaver. For example, where the hydrogel crosslinker contains disulfide bonds that crosslink polymers of the hydrogel, the cleaver can be a reducing agent, such as DTT. In some examples, the hydrogel crosslinker contains 1,2-diol bond that can be cleaved by an oxidizing agent, a strong base, or a strong acid, such as sodium periodate and periodic acid. In some examples, the hydrogel crosslinker contains a photo-cleavable moiety, the cleavage of which un-crosslinks the hydrogel matrix. In such examples, the hydrogel matrix can be exposed to light of an appropriate wavelength to cleave the photo-cleavable moiety and degrade the hydrogel matrix.

In some examples, the hydrogel precursor solution further comprises a gelation initiator. In such examples, the presence of the initiator in the hydrogel precursor solution does not induce gelation for at least a period of time sufficient to prepare the hydrogel precursor solution and flow the solution through the microfluidic droplet generator to form the monodisperse droplets. Any suitable gelation initiator can be included in the hydrogel precursor solution.

In a non-limiting example, the hydrogel precursor solution comprises acrylamide as the hydrogel polymer, N,N'-methylenebisacrylamide (Bis-acrylamide) as the hydrogel crosslinker, and potassium persulfate (KPS) as the gelation initiator. The KPS initiates a chemical reaction between the acrylamide monomers and the Bis-acrylamide. However, in the absence of a suitable catalyst (such as TEMED), gelation is delayed for at least a period of time sufficient to prepare the hydrogel precursor solution and flow the solution through the microfluidic droplet generator to form the monodisperse droplets. In this example, aqueous droplets of the hydrogel precursor solution formed using the disclosed method are contacted at an appropriate time with a suitable gelation catalyst (such as TEMED) the polymerization reaction to form hydrogel beads.

In some examples, the hydrogel precursor solution is less dense than the corresponding reservoir fluid. This creates a buoyancy force on droplets of the hydrogel precursor solution forming at the step gradient in height at the intersection of the microchannel and sample reservoir that promotes step-emulsification of the droplet and also clearance of the droplets from the reservoir end of the microchannel.

In some examples, genetic material (such as single cells or genomic DNA or cell lysate containing genomic DNA) is included in the hydrogel precursor solution to produce hydrogel beads that encapsulate the genetic material. The beads containing encapsulated genomic material can be used, for example, in sequencing assays.

Non-limiting examples of genetic material that can be encapsulated within the hydrogel beads include DNA, such as genomic or cDNA; RNA, such as mRNA, sRNA or rRNA; or a hybrid of DNA and RNA.

Example biological samples from which genetic material can be obtained include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Genetic material can also be obtained from a prokaryote such as a bacterium, *Escherichia coli, Staphylococci* or *Mycoplasma pneumoniae*; an archae; a virus such as Hepatitis C virus or human immunodeficiency virus; or a viroid. The genetic material can be obtained from a homogeneous culture or population of the above organisms or alternatively from a collection of several different organisms, for example, in a community or ecosystem. Genetic material need not be obtained from natural sources and can instead be synthesized using known techniques.

In some examples, single cells can be included in the hydrogel precursor solution for subsequent encapsulation within the hydrogel beads. Following bead production, nucleic acid molecules (for example, genomic DNA) can subsequently be isolated from the encapsulated single cells using an in-bead isolation assay.

In some examples, cell lysate can be included in the hydrogel precursor solution for subsequent encapsulation within the hydrogel beads. Following bead production, nucleic acid molecules (for example, genomic DNA) can be prepared from the encapsulated cell lysate The hydrogel beads can include any amount of genetic material that is appropriate for downstream methods. In some examples, the amount of genetic material within a bead can be controlled by diluting or concentrating the genetic material within the hydrogel precursor solution. Any suitable number of target nucleic acid molecules of any suitable length can be encapsulated in the hydrogel beads. In some examples, the encapsulated nucleic acid molecules are up to about 3 Mbases in length. In some examples, the hydrogel beads encapsulate an average of 1-1000 target nucleic acid molecules that are from about 1,000 to about 500,000 nucleotides in length.

In some examples, transposomes are bound to the genomic material (e.g., genomic DNA) before mixing the genomic material with the hydrogel precursor solution to encapsulate the material in the hydrogel beads. This can be accomplished, for example, by reacting the genomic material with Tn5 transposase in the absence of catalytic metal ion $Mg^{2+}$ (e.g., as described in the U.S. Patent Pub. 2015/0368638 of Gunderson et al., which is incorporated by reference herein in its entirety). In some examples, after the pre-tagmented DNA is encapsulated in the hydrogel beads, they are captured on a flow cell surface and buffer containing $Mg^{2+}$ ions is flowed into the flow cell to complete the tagmentation process. This is followed by extension or gap-fill/ligation reaction to complete the addition of adapters to the DNA fragment to generate the sequencing library.

Gelation of Hydrogel Beads

In implementations of the disclosed method that comprise production of hydrogel beads, the monodisperse droplets of the hydrogel precursor solution prepared using the disclosed method are incubated under conditions sufficient to induce gelation of the droplets to form hydrogel beads.

In some examples, the monodisperse droplets of the hydrogel precursor solution are contacted with a gelation initiator, gelation catalyst, or gelation initiator and gelation catalyst, to induce gelation to form the hydrogel beads. Any appropriate gelation initiator and/or gelation catalyst can be used in implementations of the method provided herein. Typically, the gelation initiator and gelation catalyst are selected based on the hydrogel precursor solution used in the method.

In some implementations, the reservoir fluid contains a sufficient concentration of gelation initiator, gelation catalyst, or gelation initiator and catalyst, to induce gelation of the monodisperse droplets of the hydrogel precursor solution, and the droplets undergo gelation in the reservoir fluid.

In other implementations, the reservoir fluid does not contain the gelation initiator, gelation catalyst, or gelation initiator and catalyst, and the reservoir fluid containing the monodisperse droplets of the hydrogel precursor solution is removed from the microfluidic device to a container with the sufficient concentration of gelation initiator, gelation catalyst, or gelation initiator and catalyst to induce gelation of the monodisperse droplets.

In some examples where the hydrogel precursor solution is agarose-based, the hydrogel precursor solution is heated prior to flow through the microfluidic droplet generator (which may also be heated to maintain the hydrogel precursor solution in a sol state). The temperature of the droplets of the hydrogel precursor solution subsequently is allowed to fall below the gelation temperature of the agarose-based hydrogel precursor solution to induce gelation of the hydrogel beads.

In some implementations the hydrogel precursor solution contains all the components necessary for forming a hydrogel except a gelation catalyst, and the monodisperse droplets are contacted with a gelation catalyst to initiate gelation of the droplets to form the hydrogel beads. Any suitable method can be used to contact the monodisperse droplets of the hydrogel precursor with the gelation catalyst. In some examples, the gelation catalyst is included in the reservoir fluid and the monodisperse droplets of the hydrogel precursor contact the gelation catalyst upon formation in the reservoir fluid. In another example, the reservoir fluid containing the monodisperse droplets of the hydrogel precursor is collected from the sample reservoir and transferred to a container, and the gelation catalyst is added to the container to induce gelation of the hydrogel beads.

In a non-limiting example, the hydrogel precursor solution comprises acrylamide as the hydrogel polymer, N,N'-methylenebisacrylamide (Bis-acrylamide) as the hydrogel crosslinker, and potassium persulfate (KPS) as the gelation initiator. The KPS initiates a chemical reaction between the acrylamide monomers and the Bis-acrylamide. However, in the absence of a suitable catalyst (such as TEMED), gelation is delayed for at least a period of time sufficient to prepare the hydrogel precursor solution and flow the solution through the microfluidic droplet generator to form the monodisperse droplets. In this example, aqueous droplets of the hydrogel precursor solution formed using the disclosed method are contacted at an appropriate time with a suitable gelation catalyst (such as TEMED) the polymerization reaction to form hydrogel beads.

Additional Description of Hydrogel Beads Produced Using the Disclosed Method

In some examples, the hydrogel beads formed using the disclosed method include 60-90% fluid, such as water, and 10-30% polymer. In certain examples, the water content of hydrogel beads is about 70-80%. In some examples, the hydrogel beads are biocompatible in that they are not toxic to living cells, and allow sufficient diffusion of oxygen and nutrients to the entrapped cells to maintain viability. In some examples, the hydrogel beads are degradable hydrogel beads that can be selectively de-polymerized. The de-polymerization reduces or destroys the lattice structure of the hydrogel bead, which increases porosity to an extent that large nucleic acid molecules (e.g., greater than 1 kb) can diffuse through the hydrogel. The degradation time is a function of polymer composition and morphology.

Crosslinking the polymers of the hydrogel beads forms a hydrogel matrix having pores (for example, a porous hydrogel matrix). These pores are capable of retaining sufficiently large genetic material within the hydrogel beads, but allow small materials, such as reagents, to pass through the pores, thereby passing in and out of the hydrogel beads. The hydrogel beads can have any pore size having a diameter sufficient to allow diffusion of reagents through the bead while retaining the encapsulated nucleic acid molecules.

As used herein, the term "reagent" refers to an agent or a mixture of two or more agents useful for reacting with, interacting with, diluting, or adding to a sample, and may include, for example, agents used in nucleic acid amplification, tagmentation, and sequencing reactions, including, for example buffers, chemicals, enzymes, polymerase, primers having a size of less than 50 base pairs, template nucleic acids, nucleotides, labels, dyes, or nucleases. In some examples, the reagent includes lysozyme, proteinase K, random hexamers, polymerase (for example, Φ29 DNA polymerase, Taq polymerase, Bsu polymerase), transposase (for example, Tn5), primers (for example, P5 and P7 adapter sequences), ligase, catalyzing enzyme, deoxynucleotide triphosphates, buffers, or divalent cations. In some examples, reagents can include lysis agents, nucleic acid purification agents, DNA amplification agents, tagmentation agents, PCR agents, or other agents used in processing of genetic materials.

The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. The size of the pores can change depending on the water content of the hydrogel beads. In some examples, the pores have a diameter of from about 10 nm to about 100 nm.

In some examples, the pore size of the hydrogel beads is tuned by varying the ratio of the concentration of polymer to the concentration of hydrogel crosslinker. In some examples, the ratio of polymer to hydrogel crosslinker is about 30:1, about 25:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:15, about 1:20, or about 1:30, or a ratio within a range defined by any two of the aforementioned ratios. In some examples, additional functions such as DNA primer, or charged chemical groups can be grafted to polymer matrix to meet the requirements of different applications.

In some examples, the porosity of the hydrogel beads may range from about 50% to about 99%, from about 75% to about 99%, or from about 80% to about 95%. Hydrogel porosity is the fractional volume (dimension-less) of a hydrogel that is composed of open space, for example, pores or other openings. Therefore, porosity measures void spaces in a material and is a fraction of volume of voids over the total volume, as a percentage between 0 and 100% (or a fraction between 0 and 1).

The hydrogel beads formed using the disclosed method can have any diameter appropriate for an intended downstream use of the beads. The diameter of the beads correlates with the cross-sectional area of the reservoir end of the microchannel in the microfluidic droplet generator. In some examples, the hydrogel beads have a diameter of from about 30 µm to about 150 µm. In some examples, the hydrogel beads have a diameter of about 2, about 3, about 4, about 5, about 10, about 15, about 20, about 30, about 40, about 50, about 60, about 70, about 80, about 90, about 100, about 110, about 120, about 130, about 140, or about 150 µm. In some examples, the hydrogel beads have a diameter of 2, 3, 4, 5, 10, 15, 20, 30, 40, 50, 60, 70, 80, 90, 100, 110, 120, 130, 140, or 150 µm, or a size within a range defined by any two of the aforementioned values. In some examples, the size of the beads is non-uniform, and thus, the size of the beads includes beads of various diameters.

Following production of the hydrogel beads using the method provided herein, the hydrogel beads are typically washed with aqueous buffer, and stored or further processed.

In some examples, the hydrogel beads are modified to contain one or more capture agents on the surface of the beads. As used herein, a "capture agent" is a material, chemical, molecule or moiety thereof that is capable of attaching, retaining or binding to a target molecule (e.g. a target nucleic acid). Example capture agents include, without limitation, a capture nucleic acid (also referred to herein as a capture oligonucleotide) that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

In some examples, the hydrogel beads are modified to contain a capture agent for immobilizing the beads on the surface of a sequencing flow cell. Examples of such capture agents include, without limitation, a capture nucleic acid that is complementary to at least a portion of a nucleic acid on the surface of the flow cell, or a member of a receptor-ligand binding pair (e.g. avidin, streptavidin, biotin, lectin, carbohydrate, nucleic acid binding protein, epitope, antibody, etc.) that binds to the other member of the pair that is localized to the surface of the sequencing flow cell. In some examples, the capture agent is a first member of a specific binding pair that is located on the hydrogel bead, and binds to a second member of the specific binding pair located on the sequencing flow cell.

In some examples, the hydrogel beads produced using the disclosed method are subsequently functionalized to contain transposomes on the bead surface, or within the beads.

As used herein, a "transposome" or "transposome complex" refers to an integration enzyme and a nucleic acid including an integration recognition site. A transposome complex is a functional complex formed by a transposase and a transposase recognition site that is capable of catalyzing a transposition reaction (see, for instance, Gunderson et al., WO 2016/130704). Examples of integration enzymes include, but are not limited to, an integrase or a transposase. Examples of integration recognition sites include, but are not limited to, a transposase recognition site.

The transposome-modified beads can be used, for example, in bead-linked tagmentation (BLT) assays for sequencing procedures. Linkage of transposomes to the bead surface can be accomplished using any suitable method, for example by functionalizing the bead surface with avidin (or an analogue thereof, such as streptavidin), and then capturing biotinylated transposomes on the functionalized bead surface.

As used herein, "tagmentation" refers to modification of a nucleic acid molecule by a transposome complex to fragment the nucleic acid molecule and ligate adapters to the 5' and 3' ends of the fragments in a single step. Tagmentation reactions can be used for preparation of sequencing libraries. Tagmentation reactions combine random fragmentation and adapter ligation into a single step to increase the efficiency of the sequencing library preparation process.

WORKING EXAMPLES

The following examples are provided to illustrate particular features of certain examples, but the scope of the claims should not be limited to those features exemplified.

Example 1

Microfluidic Droplet Generator

This example illustrates microfluidic droplet generators for use in the method of producing aqueous droplets provided herein.

Figure 16A:
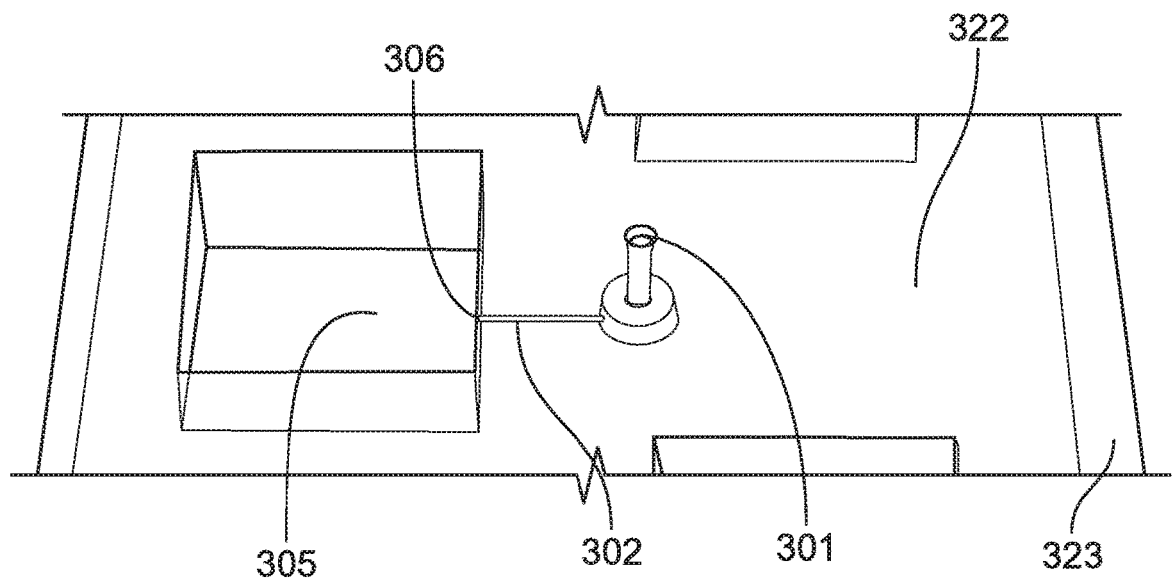
FIGS. 16A and 16B are photographs of microfluidic droplet generators designed for use in the method provided herein.

A first microfluidic droplet generator was constructed from a block of PDMS fabricated to have a single inlet fluidly connected to a single microchannel fluidly connected to a single sample reservoir when mounted on a glass plate. The inlet 301, microchannel 302, and sample reservoir 305 were milled into a planar surface of the PDMS block 322 that was about 1 cm in height, with the sample reservoir 305 and inlet 301 passing through the height of the block, and the microchannel milled into the surface. The PDMS block 322 was subsequently mounted on the glass plate 323 to define the lower surface (or floor) of the sample reservoir 305 and microchannel 302. The microchannel 302 intersects a sidewall of the sample reservoir 305 adjacent to the floor of the sample reservoir 305. The height and width of the microchannel (including the reservoir end of the microchannel) were 60 µm and 100 µm, respectively. The inlet was a straight cylindrical-shaped line that was 1 mm in diameter and intersected by (and fluidly connected to) the microchannel. The elasticity of the PDMS device allows for the tip of a typical pipette tip to be tightly inserted into the inlet to inject a solution into the microfluidic droplet generator. A photo of the microfluidic droplet generator with several elements marked is provided in FIG. 16A.

Figure 16B:
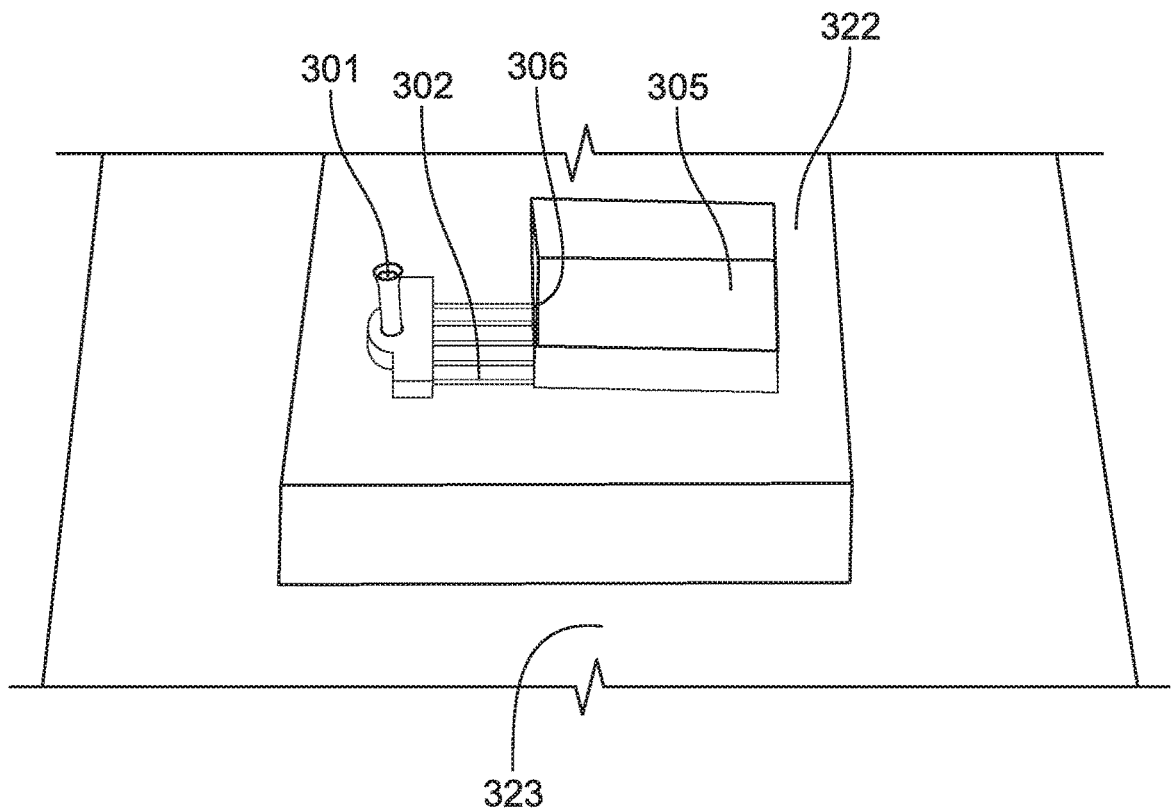

A second microfluidic droplet generator was constructed from a block of PDMS 322 fabricated to have a single inlet 301 fluidly connected to five microchannels 302 (via a chamber) that are fluidly connected to a single sample reservoir 305 when mounted on a glass plate 323. The inlet 301, chamber, microchannels 302, and sample reservoir 305 were milled into a planar surface of the PDMS block 322 that was about 1 cm in height, with the sample reservoir and inlet passing through the height of the block, and the microchannels milled into the surface. The PDMS block was subsequently mounted on the glass plate to define the lower surface (or floor) of the sample reservoir and microchannels. The microchannels intersect a sidewall of the sample reservoir adjacent to the floor of the sample reservoir. The height and width of the microchannels (including the reservoir end of the microchannel) were 60 µm and 100 µm, respectively. The inlet is a straight cylindrical-shaped line 1 mm in diameter that intersects a roof of the chamber. The five microchannels intersect a sidewall of the chamber. The elasticity of the PDMS device allows for the tip of a typical pipette tip to be tightly inserted into the inlet to inject a solution into the microfluidic droplet generator. A photo of the microfluidic droplet generator with several elements marked is provided in FIG. 16B.

Example 2

Production of Hydrogel Beads

Figure 17:
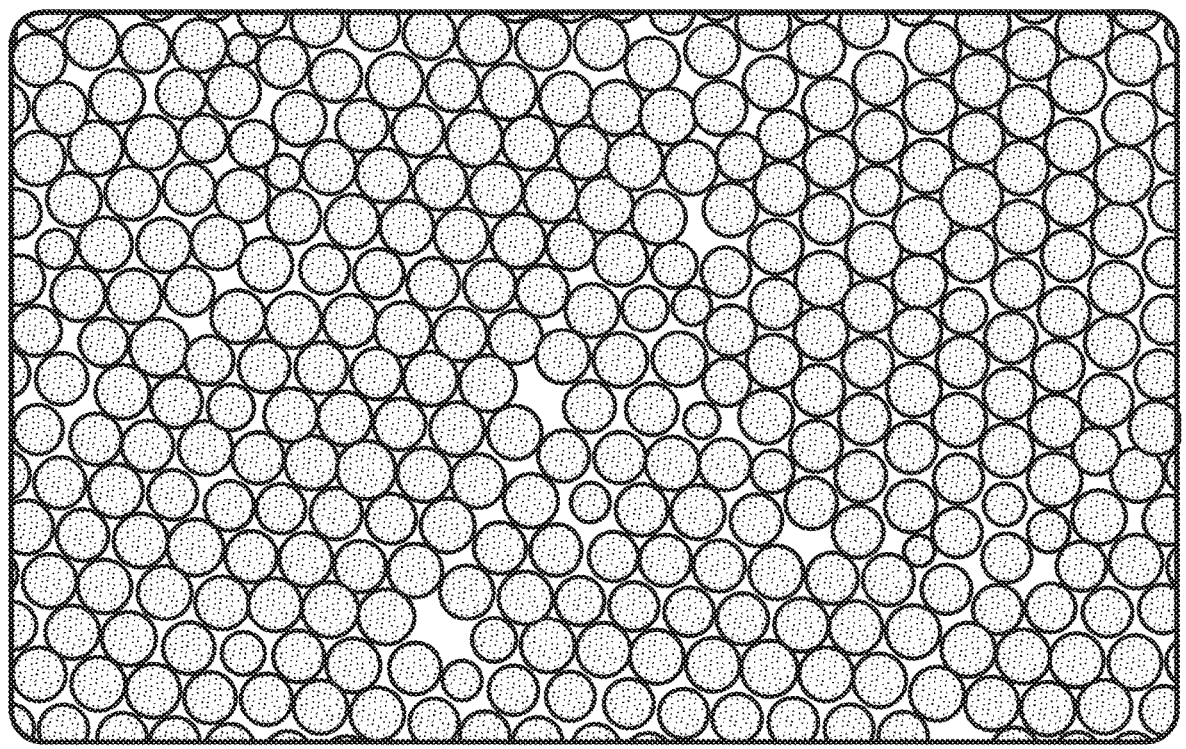
FIG. 17 is a micrograph of hydrogel beads produced using an implementation of the method for producing aqueous droplets provided herein, wherein the method further comprises producing hydrogel beads.

The utility of the microfluidic droplet generator with a single microchannel described in Example 1 for producing hydrogel beads was assessed. The sample reservoir was filled with a fluoridated oil/surfactant mixture containing gelation catalyst (TEMED) at a ratio of 600:25 v/v. The fluoridated oil/surfactant mixture was QX200™ Droplet Generation Oil commercially available from Bio-Rad (No. 1864005). 70 µL of hydrogel precursor solution containing 10.13% w/v acrylamide monomers, 0.53% w/v N,N'-methylenebisacrylamide (Bis-acrylamide), and 5.22 mg/mL of potassium persulfate was loaded into a pipette tip connected to an electronic micropipette. The pipette tip was inserted into the inlet of the microfluidic droplet generator, and the electronic micropipette was activated to expel the hydrogel precursor solution through the inlet and microchannel and into the sample reservoir. The hydrogel precursor solution formed droplets by step emulsification at the intersection of the reservoir end of the microchannel and the sample reservoir, and gelled into hydrogel beads in the presence of the hydrogel crosslinker. Subsequently, the beads were collected, washed, and assessed for size and uniformity. The resulting hydrogel beads were relative uniform in diameter with an average diameter of 123±6 µm (see FIG. 17).

Example 3

Production of Hydrogel Beads

This example illustrates an assessment of different flowrates and reservoir fluids for use in the disclosed method to produce hydrogel beads.

The microfluidic droplet generator with a single microchannel described in Example 1 was used to assess the impact of different flowrates and reservoir fluids on the production of hydrogel beads.

Hydrogel precursor solution composed of 10.13% w/v acrylamide monomers, 0.53% w/v N,N'-methylenebisacrylamide (Bis-acrylamide), and 5.22 mg/mL of potassium persulfate in water was loaded into a syringe. The syringe was in turn connected to the inlet of the microfluidic droplet generator using a 26G blunt needle (SAI Infusion Technologies, catalog number B26-100) and microtubing (Scientific Commodities, Inc, catalog number BB31695-PE/2), which was inserted into the inlet of the microfluidic droplet generator. The syringe was loaded onto a syringe pump (Harvard Apparatus, catalog number 70-4500). The syringe pump was used to push the syringe to expel the hydrogel precursor solution from the syringe and into the inlet, through the microchannel, and into the sample reservoir, at a relatively slow rate (1 µL/min) or a relatively fast rate (5 µL/min).

The reservoir fluid used in the assays included oil, surfactant, and gelation catalyst TEMED (which was added either before or after droplet production).

For assays wherein the gelation catalyst was added to the reservoir fluid in advance of droplet production ("one-step" bead production), the reservoir fluid assessed included:

1) a mixture of two fluorinated oils ("Mixed Oil"): (1,1,2,2,3,3,4,4,4-Nonafluoro-N-(nonafluorobutyl)-N-(1,1,2,2-tetrafluoroethyl)-1-butanamine; CAS No. 86508-42-1; commercially available from Sigma-Aldrich as "FC-40") and 3-ethoxyperfluoro(2-methylhexane) (CAS No. 297730-93-9, commercially available from 3M as "Novec-7500") further containing a fluorosurfactant (RAN Biotechnologies 008). The mixed oil contained FC-40 with 8% v/v Novec-7500) and 2% v/v fluorosurfactant;

2) a single fluorinated oil (Novec-7500) further containing 2% v/v fluorosurfactant (RAN Biotechnologies 008); or 3) QX200™ Droplet Generation Oil commercially available from Bio-Rad (No. 1864005).

In the one-step bead production assays, TEMED was included in the reservoir fluid at an oil-TEMED ratio (v/v) of 600:25.

For assays wherein the gelation catalyst was added to the reservoir fluid after droplet production ("two-step" bead production), the reservoir fluid assessed included:

1) "Mixed Oil" as described above;

2) Novec-7500 further containing 4% v/v fluorosurfactant (RAN Biotechnologies 008); or 3) QX200™ Droplet Generation Oil, commercially available from Bio-Rad (No. 1864005).

In the two-step bead production assays, the monodisperse droplets formed in the sample reservoir were collected, transferred to a container, and TEMED was added at an oil-TEMED ratio (v/v) of 600:50. Preliminary testing of the two-step bead production assay showed that a ratio of 600:50 v/v oil/TEMED produced hydrogel beads with a significant reduction in bead diameter variance compared to a ratio of 600:25 v/v oil/TEMED. Additionally, preliminary testing of the two-step bead production assay with Novec-7500 alone as the oil in the reservoir fluid showed that a fluorosurfactant level of 4% provided a significant increase in monodispersity of the resulting hydrogel beads compared to 2% fluorosurfactant.

Assay measurements included (1) the diameter of droplets of hydrogel precursor solution (before gelation) formed by step-emulsification after passing through the microchannel and into the sample reservoir of the microfluidic droplet generator, (2) the diameter of hydrogel beads formed after exposure to the gelation catalyst for 15 minutes, and (3) the diameter of the hydrogel beads after washing in aqueous solution to remove reservoir fluid. The aqueous wash buffer was PR2 buffer (commercially available from Illumina).

Figure 18:
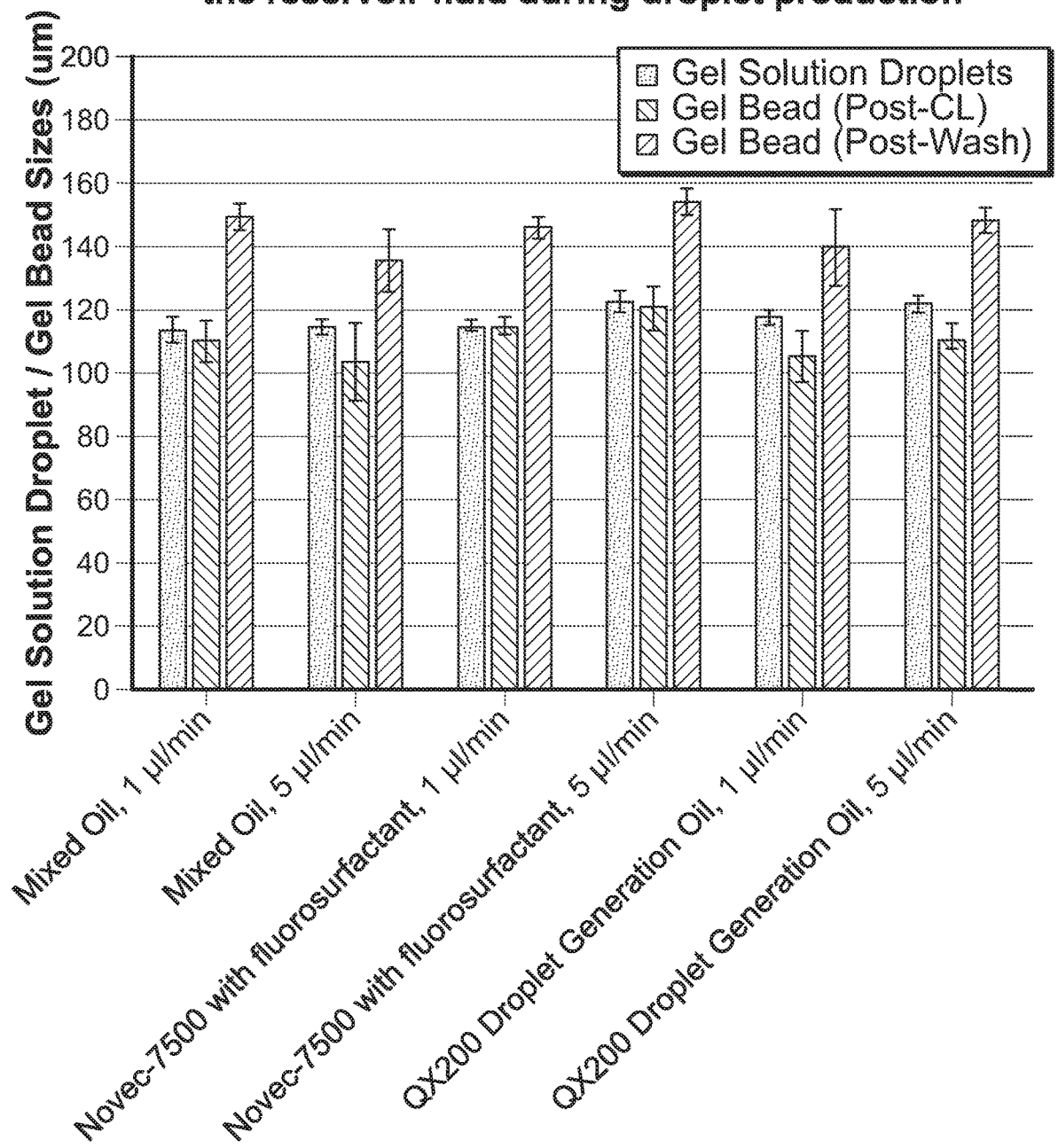
FIG. 18 is graph showing the diameter of droplets of hydrogel precursor solution and corresponding hydrogel beads produced using implementations of the method provided herein using two different flowrates and three different reservoir fluids.

Results of the "one-step" assay method are presented in FIG. 18. Diameter is shown for droplets of hydrogel precursor solution ("Gel Solution Droplets"), hydrogel beads after crosslinking and before washing ("Post-CL"), and hydrogel beads after crosslinking and washing in aqueous buffer ("Post-Wash"). As shown, bead production using each of the assessed reservoir fluid solutions resulted in hydrogel beads with relatively uniform diameter. The observed beads were also found to be generally monodisperse. It is observed that the size of gel solution droplets undergoes a reduction during the crosslinking process (upon bead formation), and a subsequent increase after washing with aqueous buffer.

Figure 19:
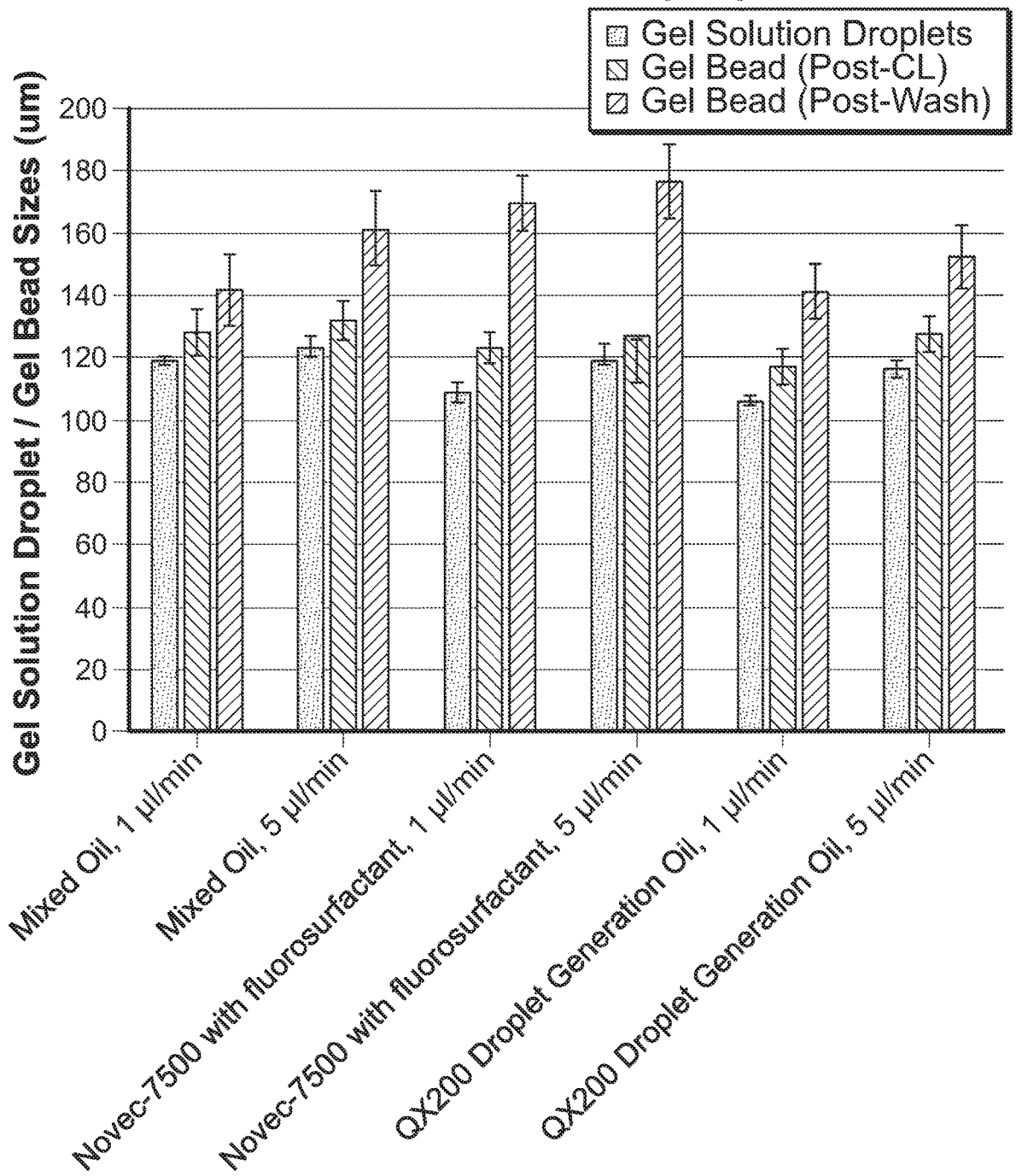
FIG. 19 is graph showing the diameter of droplets of hydrogel precursor solution and corresponding hydrogel beads produced using implementations of the method provided herein using two different flowrates and three different reservoir fluids.

Results of the "two-step" assay method are presented in FIG. 19. Diameter is shown for droplets of hydrogel precursor solution ("Gel Solution Droplets"), hydrogel beads after crosslinking and before washing ("Post-CL"), and hydrogel beads after crosslinking and washing in aqueous buffer ("Post-Wash"). As shown, bead production using the "mixed oil" reservoir fluid resulted in a significant increase in bead diameter relative to the one-step assay, as did the reservoir fluid containing Novec-7500 with 4% fluorosurfactant.

The results obtained using the one- and two-step assays show that there is little dependence on flowrates in the 1-5 µL/min range, which will facilitate tolerance of variability due to using different pipettes/users.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the singular forms "a," "an," and "the," refer to both the singular as well as plural, unless the context clearly indicates otherwise. The term "comprising" is intended to be open-ended and does not exclude additional, unrecited elements or method steps. Reference throughout this specification to "one example," "an example," "certain examples," or "some examples," etc., means that a particular feature, configuration, composition, or characteristic described in connection with the example is included in at least one example of the disclosure. Thus, the appearances of such phrases in various places throughout this specification are not necessarily referring to the same example of the disclosure.

The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. Unless context indicates otherwise, the recitations of numerical ranges by endpoints include all numbers subsumed within that range (e.g., 1 to 5 includes 1, 1.5, 2, 2.75, 3, 3.80, 4, 5, etc.).

All combinations of the foregoing concepts and all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

For any method disclosed herein that includes discrete steps, the steps may be conducted in any feasible order. And, as appropriate, any combination of two or more steps may be conducted simultaneously. Furthermore, the particular features, configurations, compositions, or characteristics may be combined in any suitable manner in one or more examples.

It will be apparent that the precise details of the disclosed method and device may be varied or modified without departing from the spirit of the described examples. We claim all such modifications and variations that fall within the scope and spirit of the claims below.

It is claimed:
1. A method, comprising:
providing a microfluidic droplet generator comprising:
a body having a single inlet fluidly connected to a microchannel fluidly connected to a sample reservoir, wherein:
the sample reservoir comprises a floor and a sidewall coupled to and extending outward from the floor, and contains a reservoir fluid that is immiscible in water;
the microchannel comprises an inlet end and a reservoir end; and
the reservoir end of the microchannel intersects the sidewall of the sample reservoir at a location that is submerged beneath the reservoir fluid and is spaced from the floor; and
flowing an aqueous solution into the single inlet, through the microchannel, and into the sample reservoir by applying pressure at the single inlet, wherein monodisperse droplets of the aqueous solution form by step-emulsification at a step change in height at the intersection of the reservoir end of the microchannel and the sidewall of the sample reservoir.

2. The method of claim 1, wherein the pressure at the single inlet is applied with a manual or electric air-displacement micropipette.

3. The method of claim 1, wherein the pressure at the single inlet is constant or varying pressure of up to about 2000 Pa.

4. The method of claim 1, wherein the flow rate of the aqueous solution at the reservoir end of the microchannel is from about 0.5 µL/min to about 5 µL/min.

5. The method of claim 1, wherein the microchannel and the sample reservoir are a single microchannel and a single sample reservoir, respectively.

6. The method of claim 1, wherein a flow axis of the aqueous solution through the reservoir end of the microchannel is parallel to the floor and perpendicular to the sidewall of the sample reservoir.

7. The method of claim 1, wherein the reservoir end of the microchannel comprises a cross-sectional area of from about 100 µm² to about 10000 µm².

8. The method of claim 1, wherein the microchannel comprises a length of at least about 100 µm from the reservoir end to the inlet end.

9. The method of claim 1, wherein a fluidic resistance of the microchannel prevents jetting of the aqueous solution into the sample reservoir at the reservoir end of the microchannel when the pressure is applied at the single inlet.

10. The method of claim 1, wherein the reservoir fluid comprises:
an oil, a viscous aqueous solution, or a combination thereof, and
a surfactant.

11. The method of claim 10, wherein:
the oil is mineral oil, silicone oil, fluorinated oil, or a combination of two or more thereof;
the viscous aqueous solution is a solution containing poly-ethylene glycol (PEG), poly-vinyl-pyrrolidone, pluronic dextran, or sucrose, or a combination of two or more thereof.

12. The method of claim 1, wherein the aqueous solution comprises genetic material, and the genetic material is encapsulated within the monodisperse droplets of the aqueous solution.

13. The method of claim 1, wherein the aqueous solution is less dense than the reservoir fluid, wherein a buoyancy force on the aqueous solution promotes formation of the monodisperse droplets at the step change in height at the intersection of the reservoir end of the microchannel and the sidewall of the sample reservoir.

14. The method of claim 1, wherein the aqueous solution is a hydrogel precursor solution, the monodisperse droplets of the aqueous solution are monodisperse droplets of the hydrogel precursor solution, and the method further comprises incubating the monodisperse droplets of the hydrogel precursor solution under conditions suitable for gelation to form hydrogel beads.

15. The method of claim 14, wherein the hydrogel precursor solution comprises hydrogel polymer and crosslinker and does not comprise a gelation catalyst for the hydrogel polymer and crosslinker; and
incubating the monodisperse droplets of the hydrogel precursor solution under conditions suitable for gelation comprises incubating the monodisperse droplets of the hydrogel precursor solution with the gelation catalyst to initiate gelation of the hydrogel polymer and crosslinker to form the hydrogel beads.

16. The method of claim 15, wherein the sample reservoir fluid comprises the gelation catalyst and the monodisperse droplets of the hydrogel precursor solution undergo gelation in the sample reservoir to form the hydrogel beads.

17. The method of claim 15, wherein:
the hydrogel precursor solution comprises acrylamide, bis-acrylamide, and potassium persulfate; and
the gelation catalyst is tetramethylethylenediamine.

18. The method of claim 14, wherein the hydrogel beads comprise pores having a diameter of sufficient size to allow diffusion of reagents through the hydrogel beads while retaining encapsulated genetic material.

19. The method of claim 14, wherein the hydrogel beads have a diameter of from about 10 µm to about 200 µm.

20. The method of claim 14, further comprising linking an outer surface of the hydrogel beads to a transposome complex.

21. The method of claim 14, wherein the hydrogel beads are degradable hydrogel beads that are degraded by:
contacting the hydrogel beads with a reagent that cleaves a reversible hydrogel crosslinker that crosslinks polymers of the hydrogel;
heating the hydrogel beads to about 90° C.;
exposing the hydrogel beads to a wavelength of light that cleaves a photo-cleavable hydrogel crosslinker that crosslinks polymer of the hydrogel; or
any combination thereof.

22. The method of claim 1, wherein the flow of the aqueous solution through the microfluidic droplet generator is not due to capillary action.

23. The method of claim 1, wherein the sidewall is a vertical sidewall and the floor of the sample reservoir is disposed vertically below the reservoir end.

24. The method of claim 1, wherein the reservoir end is disposed vertically between the floor of the sample reservoir and the single inlet.

25. The method of claim 1, wherein the sample reservoir has a constant height.

26. A method, comprising:
providing a microfluidic droplet generator comprising:
a body having a single inlet fluidly connected to a microchannel fluidly connected to a sample reservoir, wherein:
the sample reservoir comprises a floor and a sidewall, and contains a reservoir fluid that is immiscible in water;

the microchannel comprises an inlet end and a reservoir end; and the reservoir end of the microchannel intersects the sidewall of the sample reservoir at a location submerged beneath the reservoir fluid; and flowing an aqueous solution into the inlet, through the microchannel, and into the sample reservoir by applying pressure at the inlet, wherein monodisperse droplets of the aqueous solution form by step-emulsification at a step change in height at the intersection of the reservoir end of the microchannel and the sidewall of the sample reservoir;

wherein the reservoir fluid comprises:

an oil, a viscous aqueous solution, or a combination thereof, and a surfactant;

wherein:

the oil is mineral oil, silicone oil, fluorinated oil, or a combination of two or more thereof; and the viscous aqueous solution is a solution containing poly-ethylene glycol (PEG), poly-vinyl-pyrrolidone, pluronic dextran, or sucrose, or a combination of two or more thereof; and wherein the reservoir fluid comprises:

1,1,2,2,3,3,4,4,4-Nonafluoro-N-(nonafluorobutyl)-N-(1,1,2,2-tetrafluoroethyl)-1-butanamine;

3-ethoxyperfluoro(2-methylhexane); or a combination thereof.

* * * * *